US012626782B2

(12) United States Patent
Frey

(10) Patent No.: US 12,626,782 B2
(45) Date of Patent: May 12, 2026

(54) ARCHITECTURES FOR TRAINING NEURAL NETWORKS USING BIOLOGICAL SEQUENCES, CONSERVATION, AND MOLECULAR PHENOTYPES

(71) Applicant: Deep Genomics Incorporated, Toronto (CA)

(72) Inventor: Brendan Frey, Toronto (CA)

(73) Assignee: Deep Genomics Incorporated, Toronto (CA)

( * ) Notice: Subject to any disclaimer, the term of this patent is extended or adjusted under 35 U.S.C. 154(b) by 670 days.

(21) Appl. No.: 15/841,094

(22) Filed: Dec. 13, 2017

(65) Prior Publication Data

US 2018/0107927 A1 Apr. 19, 2018

Related U.S. Application Data

(63) Continuation of application No. PCT/CA2016/050689, filed on Jun. 15, 2016.
(Continued)

(51) Int. Cl.
*G16B 40/00* (2019.01)
*G06N 3/08* (2023.01)
(Continued)

(52) U.S. Cl.
CPC .............. *G06N 3/08* (2013.01); *G06N 3/084* (2013.01); *G16B 20/00* (2019.02); *G16B 20/20* (2019.02); *G16B 40/00* (2019.02); *G16B 40/20* (2019.02)

(58) Field of Classification Search
None
See application file for complete search history.

(56) References Cited

U.S. PATENT DOCUMENTS 6,128,609 A 10/2000 Rose
8,697,359 B1 4/2014 Zhang
(Continued)

FOREIGN PATENT DOCUMENTS

WO WO-9412948 A1 6/1994
WO WO-2004048511 A2 6/2004
(Continued)

OTHER PUBLICATIONS

ManChon U, Eric Talevich, Samiksha Katiyar, Khaled Rasheed, & Natarajan Kannan. Prediction and Prioritization of Rare Oncogenic Mutations in the Cancer Kinome Using Novel Features and Multiple Classifiers. Apr. 2014. Computational Biology (Year: 2014).*
(Continued)

*Primary Examiner* — Michael H Hoang
(74) *Attorney, Agent, or Firm* — WILSON SONSINI GOODRICH & ROSATI

(57) ABSTRACT

The present disclosure provides methods and systems that can ascertain how genetic variants impact molecular phenotypes. Such methods and systems may use additional conservation information. In an aspect, the present disclosure provides a method for training a molecular phenotype neural network (MPNN), comprising: (a) providing a molecular phenotype neural network (MPNN) comprising one or more parameters; (b) providing a training data set comprising (i) a set of one or more inputs comprising biological sequences and (ii) for each input in the set of one or more inputs, a set of one or more molecular phenotypes corresponding to the input; (c) configuring the one or more parameters of the MPNN based on the training data set to minimize a total loss of the training data set, thereby training the MPNN; and (d) outputting the one or more parameters of the MPNN.

22 Claims, 17 Drawing Sheets

Related U.S. Application Data

(60) Provisional application No. 62/433,664, filed on Dec. 13, 2016.

(51) Int. Cl.
| | | |
|---|---|---|
| *G06N 3/084* | (2023.01) | |
| *G16B 20/00* | (2019.01) | |
| *G16B 20/20* | (2019.01) | |
| *G16B 40/20* | (2019.01) | |

(56) References Cited

U.S. PATENT DOCUMENTS

| | | | |
|---|---|---|---|
| 9,406,017 B2 | 8/2016 | Hinton et al. | |
| 9,740,817 B1 | 8/2017 | Fernandez et al. | |
| 9,922,285 B1 | 3/2018 | Glode et al. | |
| 10,185,803 B2 | 1/2019 | Frey et al. | |
| 10,410,118 B2 | 9/2019 | Xiong et al. | |
| 11,183,271 B2 | 11/2021 | Frey et al. | |
| 11,568,960 B2 | 1/2023 | Delong et al. | |
| 2003/0122816 A1 | 7/2003 | Yu et al. | |
| 2008/0030797 A1 | 2/2008 | Circlaeys et al. | |
| 2008/0300797 A1 | 12/2008 | Tabibiazar et al. | |
| 2011/0010099 A1 | 1/2011 | Adourian et al. | |
| 2011/0172929 A1 | 7/2011 | Califano | |
| 2011/0307228 A1 | 12/2011 | Kasabov | |
| 2012/0185172 A1* | 7/2012 | Barash | G16B 20/30 |
| | | | 702/19 |
| 2012/0310539 A1 | 12/2012 | Crockett et al. | |
| 2013/0096838 A1 | 4/2013 | Fairbrother | |
| 2013/0332081 A1 | 12/2013 | Reese et al. | |
| 2014/0011977 A1 | 1/2014 | Krainer et al. | |
| 2014/0199698 A1 | 7/2014 | Rogan et al. | |
| 2014/0280327 A1 | 9/2014 | Pham et al. | |
| 2014/0359422 A1 | 12/2014 | Bassett, Jr. et al. | |
| 2015/0066378 A1 | 3/2015 | Robison et al. | |
| 2015/0100530 A1 | 4/2015 | Mnih et al. | |
| 2015/0142807 A1 | 5/2015 | Hofmann et al. | |
| 2015/0235143 A1 | 8/2015 | Eder | |
| 2016/0364522 A1 | 12/2016 | Frey et al. | |
| 2017/0024642 A1 | 1/2017 | Xiong et al. | |
| 2017/0213127 A1 | 7/2017 | Duncan | |
| 2018/0165412 A1 | 6/2018 | Frey et al. | |
| 2019/0252041 A1 | 8/2019 | Frey et al. | |
| 2019/0259473 A1 | 8/2019 | Och et al. | |
| 2020/0097835 A1 | 3/2020 | Silver et al. | |
| 2021/0383890 A1 | 12/2021 | Frey et al. | |
| 2021/0407622 A1 | 12/2021 | Frey et al. | |

FOREIGN PATENT DOCUMENTS

| | | |
|---|---|---|
| WO | WO-2012155148 A2 | 11/2012 |
| WO | WO-2013070634 A1 | 5/2013 |
| WO | WO-2016145516 A1 | 9/2016 |
| WO | WO-2016201564 A1 | 12/2016 |
| WO | WO-2017190211 A1 | 11/2017 |
| WO | WO-2017193198 A | 11/2017 |

OTHER PUBLICATIONS

Schmidt, Augusto G., et al. "An Architecture Proposal Based in Intelligent Algorithms for Motifs Discovery in Genetic Expressions." Mexican International Conference on Artificial Intelligence. Springer, Cham, 2015. https://link.springer.com/chapter/10.1007/978-3-319-27101-9_19 (Year: 2015).*

Lacey, Arron, and Xianghua Xie. Supervised Machine Learning in Bioinformatics: Protein Classification. Diss. Swansea University, 2014. https://citeseerx.ist.psu.edu/viewdoc/download?doi=10.1.1.713.9147&rep=rep1&type=pdf (Year: 2014).*

Siepel, Adam, et al. "Evolutionarily conserved elements in vertebrate, insect, worm, and yeast genomes." Genome research 15.8 (2005): 1034-1050. https://genome.cshlp.org/content/15/8/1034.short (Year: 2005).*

Kelley DR, Snoek J, Rinn JL. Basset: learning the regulatory code of the accessible genome with deep convolutional neural networks. Genome Research. May 3, 2016;26(7):990-9. https://genome.cshlp.org/content/26/7/990 (Year: 2016).*

Cheng, Shuang, et al. "MiRTDL: a deep learning approach for miRNA target prediction." IEEE/ACM transactions on computational biology and bioinformatics 13.6 (2015): 1161-1169. https://ieeexplore.ieee.org/stamp/stamp.jsp?tp=&arnumber=7362158 (Year: 2015).*

Neuneier, Ralph, and Hans Georg Zimmermann. "How to train neural networks." Neural Networks: Tricks of the Trade: Second Edition. Berlin, Heidelberg: Springer Berlin Heidelberg, 2012. 369-418. https://link.springer.com/chapter/10.1007/978-3-642-35289-8_23 (Year: 2012).*

Johansen, Morten Bo, et al. "Prediction of disease causing non-synonymous SNPs by the Artificial Neural Network Predictor NetDiseaseSNP." PloS one 8.7 (2013): e68370. https://journals.plos.org/plosone/article/file?id=10.1371/journal.pone.0068370&type=printable (Year: 2013).*

Wu, Jiaxin, and Rui Jiang. "Prediction of deleterious nonsynonymous single-nucleotide polymorphism for human diseases." The Scientific World Journal Jan. 2013 (2013): 675851. https://onlinelibrary.wiley.com/doi/epdf/10.1155/2013/675851 (Year: 2013).*

Dong, Chengliang, et al. "Comparison and integration of deleteriousness prediction methods for nonsynonymous SNVs in whole exome sequencing studies." Human molecular genetics 24.8 (2015): 2125-2137. https://academic.oup.com/hmg/article/24/8/2125/651446 (Year: 2015).*

U.S. Appl. No. 14/739,432 Notice of Allowance dated Sep. 20, 2018.

U.S. Appl. No. 14/739,432 Office Action dated Jun. 1, 2018.

Barash, et al. Deciphering the splicing code. Nature. May 6, 2010; 465 (7294):53-9. doi: 10.1038/nature09000.

Co-pending U.S. Appl. No. 15/841,106, filed Dec. 13, 2017.

Hatzigeorgiou, et al. Functional site prediction on the DNA sequence by artificial neural networks. IEEE International Joint Symposia on Intelligence and Systems, Nov. 4-5, 1996, p. 12-17, Print ISBN: 0-8186-7728-7.

Hebsgaard, et al. Splice site prediction in Arabidopsis thaliana pre-mRNA by combining local and global sequence information. Nucleic Acids Res. Sep. 1, 1996; 24(17):3439-52.

Hinton, et al. Distilling the knowledge in a neural network. arXiv preprint arXiv: 1503.02531 (2015).

Hinton, et al. Improving neural networks by preventing co-adaptation of feature detectors. arXiv preprint arXiv:1207.0580 (2012).

International Search Report corresponding to PCT/CA2016/050689; Canadian Intellectual Property Office; issued Jul. 27, 2016.

International search report dated Mar. 6, 2017 for PCT Application No. PCT/CA2016/050776.

International search report dated Dec. 22, 2016 for PCT Application No. PCT/CA2016/050510.

International Search Report for PCT/CA2016/050273, Date of Mailing Jun. 15, 2016.

Leung, et al. Deep learning of the tissue-regulated splicing code. Bioinformatics vol. 30, pp. i121-i129, Jun. 15, 2014.

Office action dated Jul. 10, 2017 for U.S. Appl. No. 14/739,432.

Quang, et al. DANN: A deep learning approach for annotating the pathogenicity of genetic variants. Bioinformatics. Mar. 1, 2015; 31(5):761-3. doi: 10.1093/bioinformatics/btu703. Epub Oct. 22, 2014.

Reese, M. G. Application of a time-delay neural network to promoter annotation in the *Drosophila melanogaster* genome. Comput Chem. Dec. 2001; 26(1):51-6.

Srivastava, et al. Dropout: a simple way to prevent neural networks from overfilling. Journal of Machine _earning Research 15.1 (2014): 1929-1958.

Written Opinion of the International Search Authority for PCT/CA2016/050273, Date of Mailing Jun. 15, 2016.

Written Opinion of the International Searching Authority corresponding to PCT/CA2016/050689; Canadian Intellectual Property Office; issued Jul. 27, 2016.

(56)           References Cited

OTHER PUBLICATIONS

Xiong, et al. The human splicing code reveals new insights into the genetic determinants of disease. Science DOI: 10.1126/science.1254806. Published Online Dec. 18, 2014.

Cerri et al. Hierarchical multi label classification using local neural networks. (2014) Journal of Computer and System Sciences, vol. 80, pp. 39-56. (Year: 2014).

Gonzalez-Recio, 0 et al. Machine learning methods and predictive ability metrics for genome wide prediction of complex traits. 2014 Livestock Science, vol. 166, pp. 217-219, plus supplemental information. (Year: 2014).

Johansen, M, B et al. Prediction of disease causing non-synonymous SNPs by the artificial neural network predictor NetDiseasesSNP. 2013 PLOS One, vol. 8 issue 7 e68730 and supplemental information. (Year: 2013).

Kelley, D. R. et al. Basset: learning the regulatory code of the accessible genome with deep convolutional neural networks. (May 3, 2016) Genome Research, vol. 26 No. 7 pp. 990-999 and some supplemental material. (Year: 2016).

Kolekar et al. alignment-free distance measure based on return time distribution for sequence analysis: applications to clustering, molecular phylogeny and subtyping. (2012) Molecular phylogenetics and Evolution. vol. 65, pp. 510-522. (Year: 2012).

Lundegaard et al. Prediction of epitopes using neural network based methods. (2011) J Immunological methods. vol. 374, pp. 26-34. (Year: 2011).

Quang et al. DanQ: a hybrid convolutional and recurrent deep neural network for quantifying the function of DNA sequences. (Apr. 15, 2016) Nucleic Acids Research vol. 44, No. 11, e107. (Year: 2016).

U.S. Appl. No. 15/841,106 Office Action dated Nov. 3, 2020.

Weissbrod et al. Multikernel linear mixed models for complex phenotype prediction. (Jun. 14, 2016) Genome Research, vol. 26, pp. 969-979. (Year: 2016).

Zhou et al. Predicting effects of noncoding variants with deep learning based sequence model. (2015) Nature Methods vol. 12, No. 10, p. 931-939. (Year: 2015).

EP16810668 Extended European Search Report dated Jan. 15, 2019.

U.S. Appl. No. 15/841,106 Notice of Allowance issued Apr. 15, 2021.

U.S. Appl. No. 15/841,106 Notice of Allowance issued Aug. 30, 2021.

Alipanahi, et al. Predicting the sequence specificities of DNA- and RNA-binding proteins by deep learning. Nature biotechnology 33.8 (2015): 831-838.

U.S. Appl. No. 15/841,106 Notice of Allowance dated Aug. 30, 2021.

U.S. Appl. No. 16/197,146 Office Action dated Apr. 3, 2023.

Basheer, Imad A., and Maha Hajmeer. Artificial neural networks: fundamentals, computing, design, and application. Journal of Microbiological Methods 43(1):3-31 (2000).

GenBank Accession No. GSE30611. Retrieved Mar. 11, 2025. Retrieved from: https://www.ncbi.nlm.nih.gov/geo/query/acc.cgi?acc=GSE30611.

Kelley et al.: Basset: learning the regulatory code of the accessible genome with deep convolutional neural networks. Genome Research. May 3, 2016; 26(7):990-9. https://genome.cshlp.org/content/26/7/990 (Year: 2016).

Lacey et al.: Supervised Machine Learning in Bioinformatics: Protein Classification. Diss. Swansea University, 2014. https://citeseerx.ist.psu.edu/viewdoc/download?doi=10.1.1.713.9147&rep=rep1&type=pdf (Year: 2014).

Libbrecht, Maxwell W., and William Stafford Noble. Machine learning applications in genetics and genomics. Nature Reviews Genetics 16(6):321-332 (2015).

Mishra, Chandrahas, and D. L. Gupta. Deep Machine Learning and Neural Networks: An overview. IAES International Journal of Artificial Intelligence 6(2):66-73 (2017).

Petrosian, Arthur et al. Recurrent neural network based prediction of epileptic seizures in intra- and extracranial EEG. Neurocomputing 30(1-4):201-218 (2000).

Schmidhuber, J. Deep learning in neural networks: An overview. Neural Networks 61(Oct. 8, 2014): 85-117.

Schmidt et al.: An Architecture Proposal Based in Intelligent Algorithms for Motifs Discovery in Genetic Expressions. Mexican International Conference on Artificial Intelligence. Springer, Cham, 2015. https://link.springer.com/chapter/10.1007/978-3-319-27101-9_19 (Year: 2015).

Sheffield, Nathan C et al. Patterns of regulatory activity across diverse human cell types predict tissue identity, transcription factor binding, and long-range interactions. Genome Research 23(5):777-788 (2013).

Siepel et al.: Evolutionarily conserved elements in vertebrate, insect, worm, and yeast genomes. Gemome Research 15(8): 1034-1050 (2005). https://genome.cship.org/content/15/8/1034.short (Year: 2005).

Subasi, Abdulhamit, and Ergun Ercelebi. Classification of EEG signals using neural network and logistic regression. Computer Methods and Programs in Biomedicine 78(2):87-99 (2005).

U.S. Appl. No. 17/369,499 Office Action dated Feb. 25, 2025.

U.S. Appl. No. 17/378,404 Office Action dated Feb. 26, 2025.

* cited by examiner

1200

Start

Encode variants
1202

Encode context
1204

Obtain variant
representations
1206

Process variants
1208

Determine link
distances
1210

End

ARCHITECTURES FOR TRAINING NEURAL NETWORKS USING BIOLOGICAL SEQUENCES, CONSERVATION, AND MOLECULAR PHENOTYPES

CROSS-REFERENCE

This application is a continuation-in-part claiming priority to PCT International Application PCT/CA2016/050689, filed Jun. 15, 2016, and U.S. Provisional Application No. 62/433,664, filed Dec. 13, 2016, each of which is entirely incorporated herein by reference.

BACKGROUND

Precision medicine, genetic testing, therapeutic development, drug target identification, patient stratification, health risk assessment and connecting patients with rare disorders can benefit from accurate information about how biological sequence variants are different or are similar in their molecular phenotypes.

Biological sequence variants, also called variants, impact function by altering molecular phenotypes, which are aspects of biological molecules that participate in biochemical processes and in the development and maintenance of human cells, tissues, and organs.

In the context of medicine and the identification and understanding of genetic variants that cause disease, exonic variants that change amino acids or introduce stop codons have traditionally been the primary focus. Yet, since variants may act by altering regulatory processes and changing a variety of molecular phenotypes, techniques that focus on relating genetic variants to changes in molecular phenotypes are valuable. Over the past decade, this has led to molecular phenotype-centric approaches that go beyond traditional exon-centric approaches. This change in approach is underscored by several observations: while evolution is estimated to preserve at least 5.5% of the human genome, only 1% accounts for exons; biological complexity often cannot be accounted for by the number of genes (e.g. balsam poplar trees have twice as many genes as humans); differences between organisms cannot be accounted for by differences between their genes (e.g. less than 1% of human genes are distinct from those of mice and dogs); increasingly, disease-causing variants have been found outside of exons.

Analyzing how variants impact molecular phenotypes is challenging. In traditional molecular diagnostics, an example workflow may be as follows: a blood or tissue sample is obtained from a patient; variants (mutations) are identified, such as by sequencing the genome, sequencing the exome; running a gene panel; or applying a microarray; the variants are manually examined for their potential impact on molecular phenotype (e.g., by a technician), using literature databases and internet search engines; and a diagnostic report is prepared. Manually examining the variants may be costly and prone to human error, which may lead to incorrect diagnosis and potential patient morbidity Similar issues may arise in therapeutic design, where there is uncertainty about the potential targets and their molecular phenotype mechanisms. Insurance may be increasingly reliant on variant interpretation to identify disease markers and drug efficacy. Since the number of possible variants may be extremely large, evaluating them manually may be time-consuming, highly dependent on previous literature, and involve experimental data that has poor coverage and therefore can lead to high false negative rates, or "variants of uncertain significance." Automating or semi-automating the analysis of variants and environmental contexts and their impact on molecular phenotypes and disease phenotypes is thus beneficial.

SUMMARY

As recognized herein, a key unmet need in precision medicine is the ability to automatically or semi-automatically analyze biological sequence variants by examining their impact on molecular phenotypes, such as, for example, determining associations between genetic variants and gross phenotypes, such as disease, using the molecular phenotypes induced by the genetic variants. To do this, it may be beneficial to develop methods and systems that can ascertain how genetic variants impact molecular phenotypes, which are intermediate biochemical attributes within cells that impact gross phenotype. The present disclosure provides methods and systems that may advantageously use such additional conservation information to increase performance and accuracy.

In one aspect, a system for linking two or more biologically related variants derived from biological sequences is provided, the system comprising: one or more molecular phenotype neural networks (MPNNs), each MPNN comprising: an input layer configured to obtain one or more values digitally representing a variant in the two or more biologically related variants; one or more feature detectors, each configured to obtain input from at least one of: (i) one or more of the values in the input layer and (ii) an output of a previous feature detector; and an output layer comprising values representing a molecular phenotype for the variant, comprising one or more numerical elements obtained from one or more of the feature detectors; and a comparator linked to the output layer of each of the one or more MPNNs, the comparator configured to compare the molecular phenotypes for pairs of variants in the biologically related variants to determine a numerical link distance for the pairs of variants.

In another aspect, a method for linking two or more biologically related variants derived from biological sequences is provided, the method comprising: obtaining at an input layer of a molecular phenotype neural network (MPNN), two or more digital representations of the two or more biologically related variants, each comprising one or more input values; processing each variant by the MPNN, the MPNN comprising one or more feature detectors configured to obtain input from at least one of: (i) the one or more of the input values of the respective variant and (ii) an output of a previous feature detector, the MPNN configured to provide output values representing a molecular phenotype for the variant, comprising one or more numerical elements obtained from one or more of the feature detectors; for each of one or more pairs of variants in the two or more biologically related variants, determining, by a comparator, a numerical link distance, the determining comprising comparing the molecular phenotypes for the pair of variants.

The system may further comprise an encoder configured to generate the digital representation of the variant, the input layer being linked to an output of the encoder.

The encoder may further be configured to generate an encoded representation of one or more contexts, wherein the input layer is configured to obtain one or more values from the encoded representation of the one or more contexts.

The input layer may additionally be configured to obtain an additional one or more values digitally representing one or more contexts, wherein the molecular phenotype further comprises one or more numerical elements for each of one or more of the one or more contexts.

For a pair of variants processed by the MPNN, the comparator may determine the numerical link distance, by, for at least one of the one or more numerical elements in the molecular phenotype, applying one of the following linear or nonlinear functions to the difference between the molecular phenotype for a first variant in the pair of variants and the molecular phenotype for a second variant in the pair of variants: the identity operation, the square operation, and the absolute operation.

At least one of the variants in the two or more biologically related variants may be obtained from: a DNA, an RNA or a protein sequence of a patient; a sequence that may result when a DNA or an RNA editing system is applied, or a protein modification system is applied; a sequence where nucleotides targeted by a therapy are set to fixed values; a sequence where nucleotides targeted by a therapy are set to values other than existing values; and a sequence where nucleotides that overlap, fully or partially, with nucleotides that are targeted by a therapy are deactivated.

The molecular phenotype may comprise one or more of the following elements: percentage of transcripts that include an exon; percentage of transcripts that use an alternative splice site; percentage of transcripts that use an alternative polyadenylation site; the affinity of an RNA-protein interaction; the affinity of a DNA-protein interaction; the specificity of a microRNA-RNA interaction; the level of protein phosphorylation.

One or more variants in the two or more biologically related variants may be labeled variants, wherein labeled variants have associated labels, and the system may further comprise a labeling unit configured to associate labels with other variants comprising at least one variant in the two or more biologically related variants that are not labeled variants.

The labeling unit may further be configured to associate each other variant with the label of the variant in the labeled variants that has the lowest link distance to the respective other variant.

The number of other variants may be at least two, the labels may be comprised of one or more numerical values, and the two or more other variants may be sorted or partially sorted using one of the one or more numerical values in the labels.

For each other variant in the other variants, the MPNN may be configured to, for each labeled variant in the labeled variants, determine a numerical weight for the other variant and the labeled variant by applying a linear or a nonlinear weighting module to the link distance for a pair of variants consisting of the other variant and the labeled variant, and the labeling unit may be configured to, for each other variant of the other variants, determine an associated label by summing terms corresponding to the labeled variants, wherein each term is obtained by multiplying the numerical weight for the other variant and the corresponding labeled variant into the label associated with the corresponding labeled variant.

The MPNN may further be configured to, for each other variant in the other variants and for each labeled variant in the labeled variants, divide the numerical weight for the other variant and the labeled variant by the sum of the weights for the other variant and the labeled variants.

The number of other variants may be at least two and the labels may be comprised of one or more numerical values, and the system may be configured to sort or partially sort the two or more other variants using one of the one or more numerical values in the labels associated with the two or more other variants.

The system may further be configured to, for each of one or more pairs of variants in the two or more biologically related variants, obtain a measure of proximity of the pair of variants within the biological sequence, wherein the determining a numerical link distance further comprises combining the measure of proximity of the pair of variants with the comparing of the molecular phenotypes for the pair of variants.

The linear or the nonlinear weighting module may determine weights differently for different values of the labels.

Comparing the molecular phenotypes for the pairs of variants may comprise obtaining a link neural network, wherein the input of the link neural network comprises the molecular phenotypes for each pair of variants and wherein the output of the link neural network is the link distance for the pair of variants; and applying the link neural network to the molecular phenotypes for the pairs of variants.

The system may further be configured to obtain additional information pertaining to the similarity of function of the pair of variants, wherein the input of the link neural network further comprises the additional information.

The parameters of the link neural network may be determined using a training procedure applied to a dataset of examples, wherein each example comprises a pair of variants and a target value for the link distance.

In another aspect, the present disclosure provides a method for training a molecular phenotype neural network (MPNN), comprising: (a) providing a molecular phenotype neural network (MPNN) comprising one or more parameters; (b) providing a training data set comprising (i) a set of one or more inputs comprising biological sequences and (ii) for each input in the set of one or more inputs, a set of one or more molecular phenotypes corresponding to the input; (c) configuring the one or more parameters of the MPNN based on the training data set to minimize a total loss of the training data set, thereby training the MPNN; and (d) outputting the one or more parameters of the MPNN.

In some embodiments, the training data set further comprises (iii) a conservation value corresponding to each of at least a portion of the set of biological sequences. In some embodiments, minimizing the total loss of the training data set is minimized based at least in part on minimizing (i) a total loss of the set of one or more molecular phenotypes or (ii) a total loss of the set of conservation values. In some embodiments, minimizing the total loss of the training data set is minimized based at least in part on minimizing (i) a total loss of the set of one or more molecular phenotypes and (ii) a total loss of the set of conservation values.

In some embodiments, the method further comprises providing a test biological sequence and using the trained MPNN to determine a molecular phenotype corresponding to the test biological sequence. In some embodiments, the method further comprises generating a conservation value corresponding to the test biological sequence. In some embodiments, the MPNN comprises a single intermediate layer configured to determine the molecular phenotype and the conservation value corresponding to the test biological sequence. In some embodiments, the MPNN comprises a plurality of intermediate layers, and the last layer of the plurality of intermediate layers is configured to determine the molecular phenotype and the conservation value corresponding to the test biological sequence. In some embodiments, the MPNN comprises a plurality of intermediate layers, wherein a first layer of the plurality of intermediate layers is configured to determine the molecular phenotype corresponding to the test biological sequence, and wherein a second layer of the plurality of intermediate layers is configured to determine the conservation value corresponding to the test biological sequence. In some embodiments, the molecular phenotype corresponding to the test biological sequence is determined based on the conservation value corresponding to the test biological sequence.

In another aspect, the present disclosure provides a system for training a molecular phenotype neural network (MPNN), comprising: a data storage unit comprising a training data set comprising (i) a set of one or more inputs comprising biological sequences and (ii) for each input in the set of one or more inputs, a set of one or more molecular phenotypes corresponding to the input; and one or more computer processors operatively coupled to the data storage unit, wherein the one or more computer processors are individually or collectively programmed to: (a) provide a molecular phenotype neural network (MPNN) comprising one or more parameters; (b) provide a training data set comprising (i) a set of one or more inputs comprising biological sequences and (ii) for each input in the set of one or more inputs, a set of one or more molecular phenotypes corresponding to the input; (c) configure the one or more parameters of the MPNN based on the training data set to minimize a total loss of the training data set, thereby training the MPNN; and (d) output the one or more parameters of the MPNN.

In some embodiments, the training data set further comprises (iii) a conservation value corresponding to each of at least a portion of the set of biological sequences. In some embodiments, the one or more computer processors are individually or collectively programmed to minimize the total loss of the training data set at least in part by minimizing (i) a total loss of the set of one or more molecular phenotypes or (ii) a total loss of the set of conservation values. In some embodiments, the one or more computer processors are individually or collectively programmed to minimize the total loss of the training data set at least in part by minimizing (i) a total loss of the set of one or more molecular phenotypes and (ii) a total loss of the set of conservation values.

In some embodiments, the one or more computer processors are individually or collectively programmed to provide a test biological sequence and use the trained MPNN to determine a molecular phenotype corresponding to the test biological sequence. In some embodiments, the one or more computer processors are individually or collectively programmed to generate a conservation value corresponding to the test biological sequence. In some embodiments, the MPNN comprises a single intermediate layer configured to determine the molecular phenotype and the conservation value corresponding to the test biological sequence. In some embodiments, the MPNN comprises a plurality of intermediate layers, wherein the last layer of the plurality of intermediate layers is configured to determine the molecular phenotype and the conservation value corresponding to the test biological sequence. In some embodiments, the MPNN comprises a plurality of intermediate layers, wherein a first layer of the plurality of intermediate layers is configured to determine the molecular phenotype corresponding to the test biological sequence, and wherein a second layer of the plurality of intermediate layers is configured to determine the conservation value corresponding to the test biological sequence. In some embodiments, the one or more computer processors are individually or collectively programmed to determine the molecular phenotype corresponding to the test biological sequence based at least in part on the conservation value corresponding to the test biological sequence.

Another aspect of the present disclosure provides a non-transitory computer-readable medium comprising machine-executable code that, upon execution by one or more computer processors, implements any of the methods above or elsewhere herein.

Another aspect of the present disclosure provides a computer system comprising one or more computer processors and a non-transitory computer-readable medium operatively coupled thereto. The non-transitory computer-readable medium comprises machine-executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

DETAILED DESCRIPTION

Figure 1A:
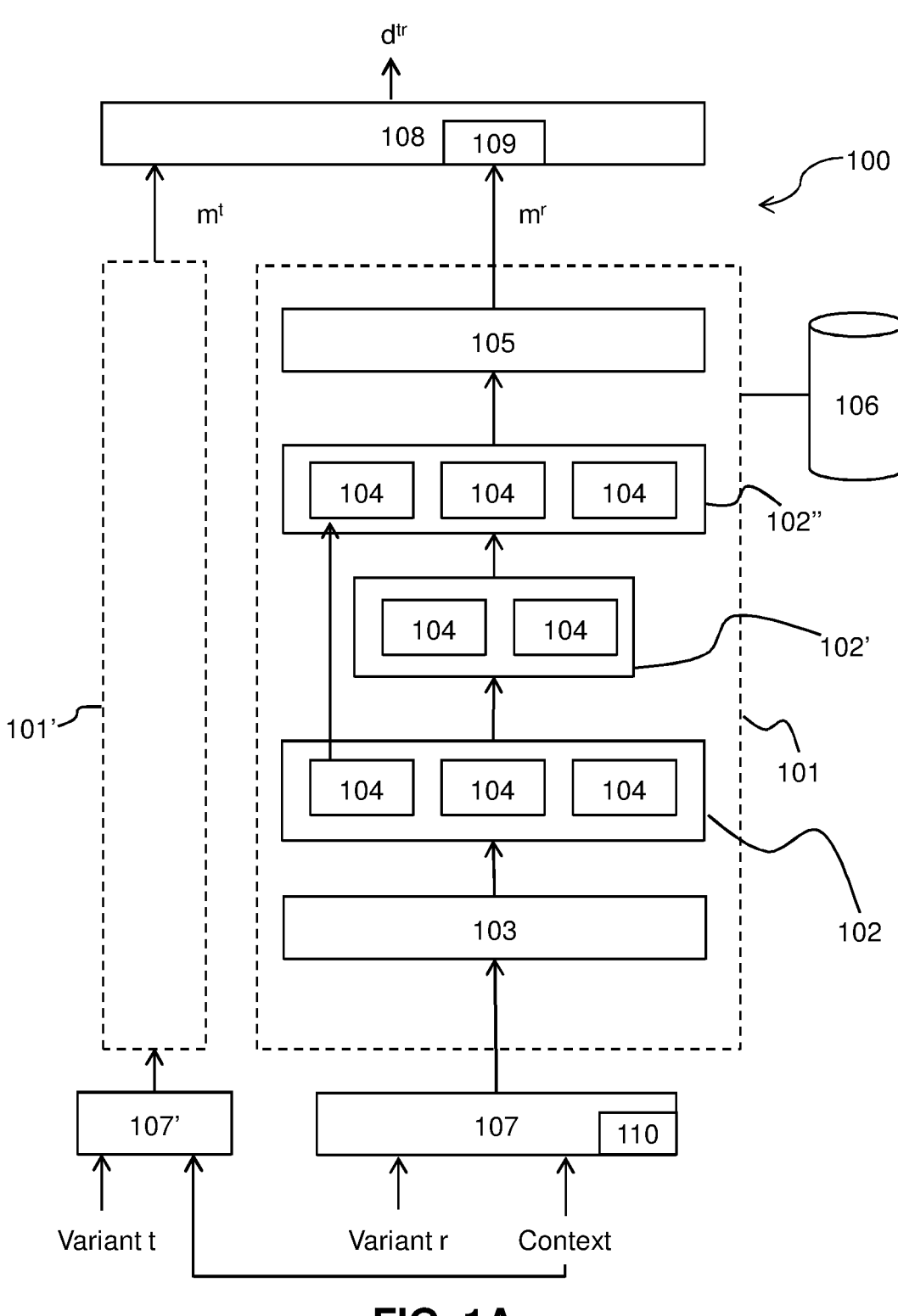
FIG. 1A is a block diagram illustrating a first embodiment of a system for linking biological sequence variants.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

The term "sequence," as used herein, generally refers to a sequence of characters. The sequence may be a biological sequence, such as a sequence of nucleic acid molecules or amino acids. The sequence of nucleic acid molecules may be part of a deoxyribonucleic acid (DNA) molecule or ribonucleic acid (RNA) molecule.

The term "variant," as used herein, generally refers to differences in a sequence as compared to a reference. Such difference may be a difference in characters. A variant may be a biological sequence variant. A variant may be a genetic variant or genetic aberration. The genetic aberration may be a nucleotide variant, single base substitution, copy number variation (CNV), single nucleotide variant (SNV), insertion or deletion (indel), fusion, transversion, translocation, inversion, duplication, amplification, or truncation.

A key unmet need in precision medicine is the ability to automatically or semi-automatically analyze biological sequence variants by examining their impact on molecular phenotypes, such as, for example, determining associations between genetic variants and gross phenotypes, such as disease, using the molecular phenotypes induced by the genetic variants. To do this, it may be beneficial to develop methods and systems that can ascertain how genetic variants impact molecular phenotypes, which are intermediate biochemical attributes within cells that impact gross phenotype. The present disclosure provides methods and systems that may advantageously use such additional conservation information to increase performance and accuracy.

The present disclosure provides systems and methods for determining links between biological sequence variants, also called variants, to other variants and generating scores for the strengths of the link between two variants according to the similarity in their molecular phenotypes. The systems generally comprise neural network architectures that are referred to herein as "molecular phenotype neural networks". The biological sequence may be a DNA sequence, an RNA sequence, or a protein sequence. Linked variants may be used in precision medicine to ascertain pathogenicity in genetic testing, to identify drug targets, to identify patients that respond similarly to a drug, to ascertain health risks, and to connect patients that have similar molecular phenotypes.

A biological sequence variant, also called a variant, as used herein, generally refers to a biological sequence, such as a DNA sequence, an RNA sequence or a protein sequence, that may be derived from an existing biological sequence through a combination of substitutions, insertions and deletions. For example, the gene BRCA1 is represented as a specific DNA sequence of length 81,189 in the reference genome. If the samples from multiple patients are sequenced, then multiple different versions of the DNA sequence for BRCA1 may be obtained. These sequences, together with the sequence from the reference genome, may form a set of variants.

To distinguish variants that are derived from the same biological sequence from those that are derived from different biological sequences, the following will refer to variants that are derived from the same biological sequence as "biologically related variants" and the term "biologically related" is used as an adjective to imply that a variant is among a set of biologically related variants. For example, the variants derived from the gene BRCA1 are biologically related variants. The variants derived from another gene, SMN1, are also biologically related variants. However, the variants derived from BRCA1 are not biologically related to the variants derived from SMN1. The term "biologically related variants" is used to organize variants according to their function, but it will be appreciated that this organization may be different according to different functions. For example, when they are transcribed, two different but homologous genes may generate the same RNA sequence. Variants in the RNA sequence may impact function in the same way, such as by impacting RNA stability. This is the case even though they originated from two different, albeit homologous, DNA sequences. The RNA sequence variants, regardless of from which gene they came, may be considered to be biologically related.

Biologically related variants may be derived naturally by DNA replication error, by spontaneous mutagenesis, by sexual reproduction; by evolution; by DNA, RNA and protein editing/modification processes, by retroviral activity, or by other approaches. Biologically related variants may be derived experimentally by plasmid construction, by gene editing systems such as CRISPR/Cas9, by sequencing samples from patients and aligning them to a reference sequence, or by other approaches. Biologically related variants may be derived computationally by applying a series of random or preselected substitutions, insertions and deletions to a reference sequence, by using a model of mutation to generate variants, or by other approaches. Biologically related variants may be derived from a DNA or RNA sequence of a patient, a sequence that may result when a DNA or RNA editing system is applied, a sequence where nucleotides targeted by a therapy are set to fixed values, a sequence where nucleotides targeted by a therapy are set to values other than existing values, or a sequence where nucleotides that overlap, fully or partially, with nucleotides that are targeted by a therapy are deactivated. It will be appreciated that there are other ways in which biologically related variants may be produced.

Depending on the function being studied, different sets of biologically related variants may be obtained from the same biological sequences. In the above example, DNA sequences for the BRCA1 gene of length 81,189 may be obtained from the reference genome and a group of patients and form a set of biologically related variants. As an example, if one is interested in how variants impact splicing of exon 6 in BRCA1, for each patient and the reference genome, a subsequence of length 600 nucleotides centered at the 3 prime end of exon 6 may be extracted. These splice site region sequences may form a different set of biologically related variants than the set of whole-gene biologically related variants.

The above discussion underscores that the functional meaning of a variant is context dependent, that is, dependent on the conditions. Consider the reference genome and an intronic single nucleotide substitution located 100 nucleotides from the 3 prime splice site of exon 6 in the BRCA1 gene. This may be viewed as two BRCA1 variants of length 81,189 nucleotides, or as two exon 6 splice site region variants of length 600 nucleotides, or, in the extreme, as two chromosome 17 variants of length 83 million nucleotides (BRCA1 is located on chromosome 17). Viewing the single nucleotide substitution in these three different situations may be important for understanding its impact on BRCA1 gene expression, BRCA1 exon 6 splicing, and chromatin interactions in chromosome 17. Furthermore, consider the same single nucleotide substitution in two different patients. Because the neighboring sequence may be different in the two patients, the variants may be different.

A variant may impact function by altering one or more molecular phenotypes, which quantify aspects of biological molecules that participate in the biochemical processes that are responsible for the development and maintenance of human cells, tissues, and organs. A molecular phenotype may be a quantity, level, potential, process outcome, or qualitative description. The term "molecular phenotype" may be used interchangeably with the term "cell variable." Examples of molecular phenotypes include the concentration of BRCA1 transcripts in a population of cells; the percentage of BRCA1 transcripts that include exon 6; chromatin contact points in chromosome 17; the strength of binding between a DNA sequence and a protein; the strength of interaction between two proteins; DNA methylation patterns; RNA folding interactions; and inter-cell signaling. A molecular phenotype can be quantified in a variety of ways, such as by using a categorical variable, a single numerical value, a vector of real-valued numbers, or a probability distribution.

Molecular phenotypes are often causally determined by biological sequences that are close to where they occur. For example, the existence or absence of a particular motif on a DNA sequence may determine if a particular DNA binding protein may bind. An exon on a precursor messenger RNA (mRNA) may be spliced out during RNA splicing depending on the combined effects of a set of intronic and exonic motifs of RNA-binding proteins within and around that exon. Understanding and modelling how biological sequences determine molecular phenotypes is viewed as a major set of goals in biological and medical research.

A variant that alters a molecular phenotype may be more likely to alter a gross phenotype, such as disease or aging, than a variant that does not alter any molecular phenotype. This is because variants generally impact gross phenotypes by altering the biochemical processes that rely on DNA, RNA and protein sequences.

Since variants can impact function by altering molecular phenotypes, a set of biologically related variants can be associated with a set of molecular phenotypes. BRCA1 whole-gene variants may be associated with the molecular phenotype measuring BRCA1 transcript concentration. BRCA1 exon 6 splice site region variants may be associated with the molecular phenotype measuring the percentage of BRCA1 transcripts that include exon 6. Chromosome 17 variants may be associated with the molecular phenotype measuring chromatin contact points in chromosome 17. This association may be one to one, one to many, many to one, or many to many. For instance, BRCA1 whole-gene variants, BRCA1 exon 6 splice region variants and chromosome 17 variants may be associated with the molecular phenotype measuring BRCA1 transcript concentration.

The association of a variant with a molecular phenotype does not imply for certain that the variant alters the molecular phenotype, it only implies that it may alter the molecular phenotype. An intronic single nucleotide substitution located 100 nucleotides from the 3 prime splice site of exon 6 in the BRCA1 gene may alter the percentage of BRCA1 transcripts that include exon 6, whereas a single nucleotide substitution located 99 nucleotides from the 3 prime splice site of exon 6 in the BRCA1 gene may not. Also, for the former case, whereas a G to T substitution may alter the molecular phenotype, a G to A substitution may not. Furthermore, the molecular phenotype may be altered in one cell type, but not in another, even if the variant is exactly the same. This is another example of context dependence.

The systems and methods described herein can be used to compare biologically related variants to one another by examining how they alter one or more associated molecular phenotypes. For example, the variants consisting of 600 nucleotides centered at the 3 prime end of exon 6 of BRCA1 obtained from a set of patients can be compared by examining how they alter the percentage of BRCA1 transcripts that include exon 6. If two variants cause the percentage of BRCA1 transcripts that include exon 6 to change in a similar way, the variants are more likely to be functionally related than if they cause the percentage of BRCA1 transcripts that include exon 6 to change in a different way.

There are different approaches to determining how variants alter the same molecular phenotype, ranging from experimental, to computational, to hybrid approaches.

Supervised learning may be used to train a machine learning model to take a biological sequence and additional input information as input and to output a label, a set of labels, or more structured information that is associated with the input sequence. The labels may correspond to molecular phenotypes. The additional input information may correspond to other "input" molecular phenotypes, or to other contextual information, such as age. Examples include predicting chromatin state from DNA sequence, predicting splice sites from DNA sequence, predicting polyadenylation sites from RNA sequence, predicting protein stability from protein sequence, predicting protein-protein interactions from protein sequences, predicting protein-DNA interactions from protein and DNA sequences, and predicting splicing patterns from protein-RNA interactions and from RNA sequence. The associated label, set of labels, or more structured information may be determined from a discrete molecular phenotype or a continuous molecular phenotype, such as the percent of transcripts with an exon spliced in, a gene expression level, or the concentration of a protein complex, or it may be determined by other approaches, such as by labeling sequences as pathogenic or non-pathogenic using clinical data.

Machine learning models that are commonly used for supervised learning in the context of biological sequences include linear regression, logistic regression, neural networks, convolutional networks, deep neural networks, recurrent neural networks, long short-term memory networks, Gaussian processes, decision trees, random forests, and support vector machines. While there are many supervised learning models, they all have in common that, for training, they require a training set consisting of biological sequences and associated labels. In some cases, the input may be multiple biological sequences, such as in the case of predicting protein-DNA interactions, where the input may be a protein sequence and a DNA sequence.

Unsupervised learning may be used to train a machine learning model to take a biological sequence as input and output a set of features that are useful in describing the input. This is called feature extraction. One of the features may be a real number that scores the sequence, using log-likelihood or squared error. Extracted features may be used for visualization, for classification, for subsequent supervised learning, and more generally for representing the input for subsequent storage or analysis. In some cases, each training case may consist of multiple biological sequences. Examples include extracting features from DNA promoter sequences, extracting features from RNA splice sites, extracting features from pairs of DNA sequences that are in chromatin contact, and extracting features from pairs of protein sequences that are in contact.

Machine learning models that are commonly used for unsupervised learning in the context of biological sequences include k-means clustering, mixtures of multinomial distributions, affinity propagation, discrete factor analysis, hidden Markov models, Boltzmann machines, restricted Boltzmann machines, autoencoders, convolutional autoencoders, recurrent neural network autoencoders, and long short-term memory autoencoders. While there are many unsupervised learning models, they all have in common that, for training, they require a training set consisting of biological sequences, without associated labels.

The present disclosure provides systems comprising structured computational architectures referred to herein as molecular phenotype neural networks (MPNNs). MPNNs are artificial neural networks, also called neural networks, which are a powerful class of architectures for applying a series of computations to an input so as to determine an output. The input to the MPNN is used to determine the outputs of a set of feature detectors, which are then used to determine the outputs of other feature detectors, and so on, layer by layer, until the molecular phenotype output is determined. An MPNN architecture can be thought of as a configurable set of processors configured to perform a complex computation. The configuration is normally done in a phase called training, wherein the parameters of the MPNN are configured so as to maximize the computation's performance on determining molecular phenotypes or, equivalently, to minimize the errors made on that task. Because the MPNN gets better at a given task throughout training, the MPNN is said to be learning the task as training proceeds. MPNNs can be trained using machine learning methods. Once configured, an MPNN can be deployed for use in the task for which it was trained and herein for linking variants as described below.

In another aspect, the present disclosure provides methods of using conservation data to train MPNNs.

A biological sequence in a specific individual or in a reference sequence for a species may be aligned to sequences from other species to determine the level of conservation of symbols within the sequence. For example, the human genome may be aligned to the genomes of other mammals to determine a conservation track, consisting of one number for each nucleotide in the human genome. A large value may indicate the nucleotide is conserved across mammals, i.e., that it has the same value. Similarly, a human protein sequence may be aligned to proteins from other mammals so as to determine the level of conservation of each amino acid in the protein sequence. Biological sequences may include DNA sequences, RNA sequences, or protein sequences among others. There may be different ways of determining conservation and of representing the conservation level for each symbol in the sequence.

It is known that highly conserved symbols within biological sequences are more likely to be functional, that is, to be important for the proper function of a living cell in the corresponding individual. For example, mutations in symbols that are highly conserved are more likely to impact phenotype, such as diseases, including cancers and neurological disorders.

Molecular phenotypes may depend on environmental context, which are referred to herein as "context." Examples of context include cell type, tissue type, age, diet, and hormone levels. Molecular phenotypes may also depend on other molecular phenotypes. For example, the concentration of BRCA1 transcripts in a population of cells depends on the concentrations of transcriptional regulation proteins in the same population of cells. The percentage of BRCA1 transcripts that include exon 6 depends on the concentrations of splicing regulation proteins in the same population of cells. To account for this, the context may sometimes include other molecular phenotypes.

Referring now to FIG. 1A, a system (100) comprises an MPNN (101) that is a neural network comprising a layer of input values that represents the variant (103) (which may be referred to as an "input layer"), one or more layers of feature detectors (102), and a layer of output values that represents the molecular phenotype (105) (which may be referred to as an "output layer"). Each layer of feature detectors (102, 102', 102") may comprise one or more feature detectors (104), wherein each feature detector comprises or is implemented by a processor. Weights may be applied in each feature detector (104) in accordance with learned weighting, which is generally learned in a training stage of the neural network. The input values, the learned weights, the feature detector outputs, and the output values may be stored in a memory (106) linked to the MPNN (101).

Figure 1B:
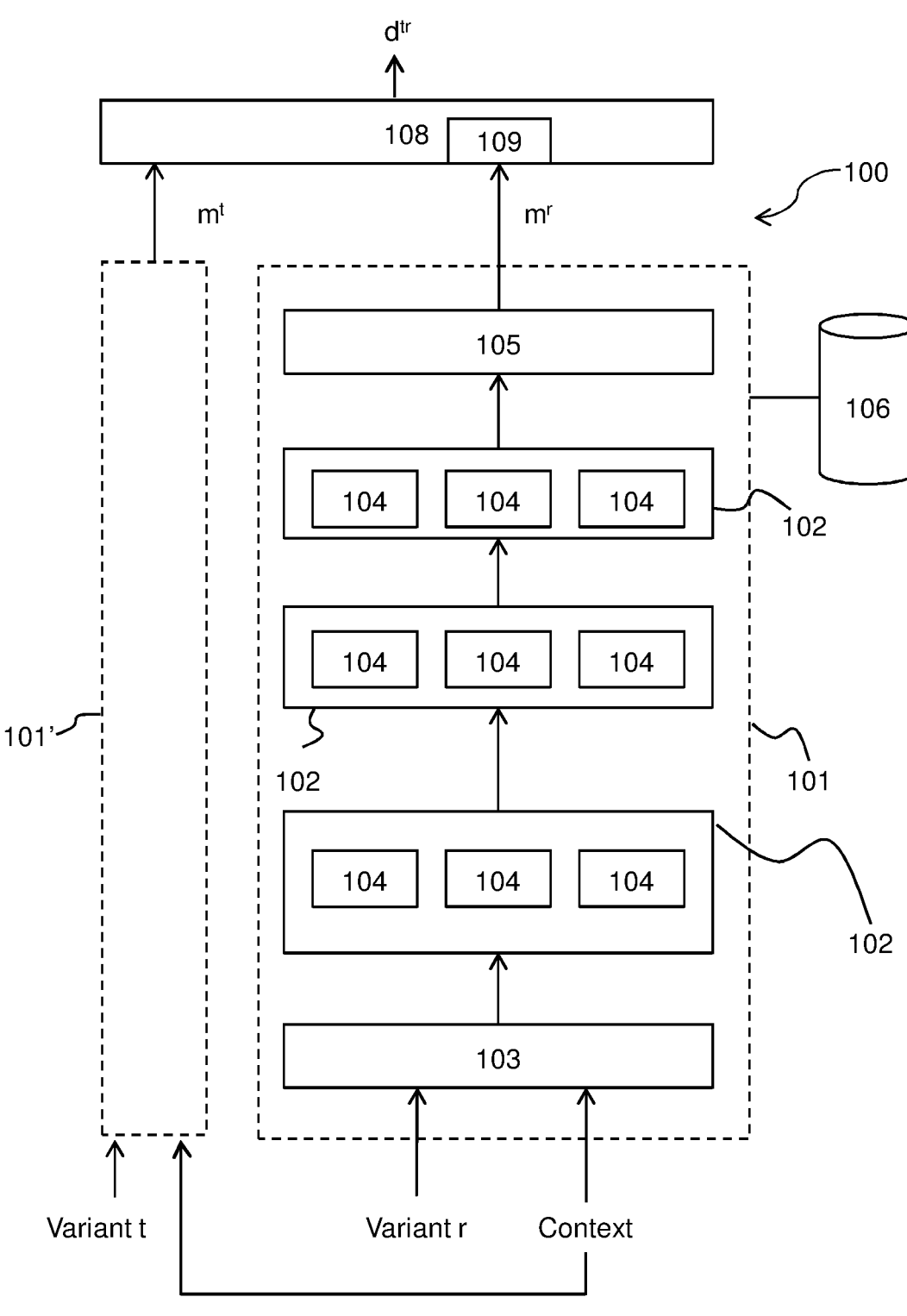
FIG. 1B is a block diagram illustrating a second embodiment of a system for linking biological sequence variants.
Figure 1C:
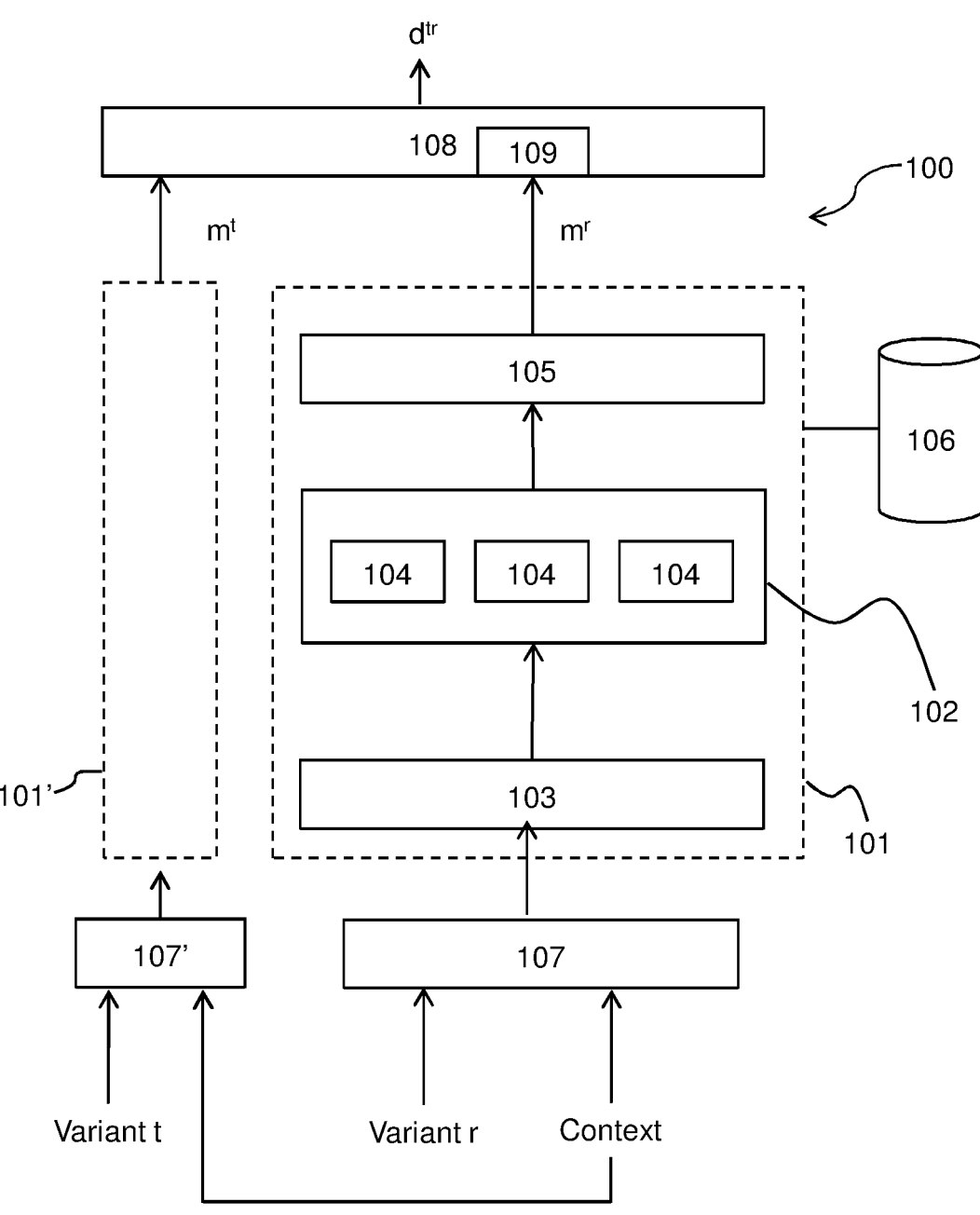
FIG. 1C is a block diagram illustrating a third embodiment of a system for linking biological sequence variants.
Figure 1D:
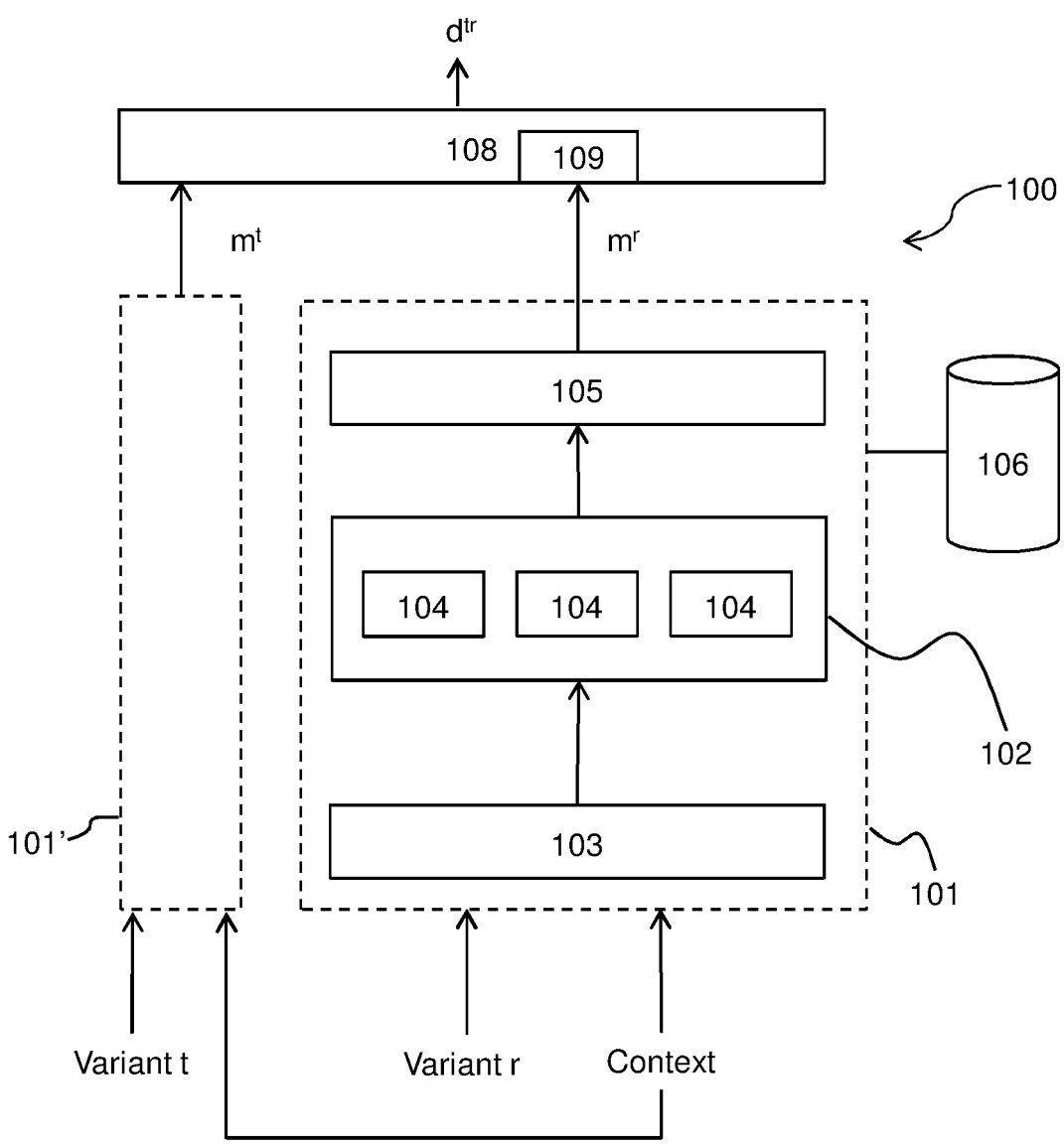
FIG. 1D is a block diagram illustrating a fourth embodiment of a system for linking biological sequence variants.

The particular MPNN (101) shown in FIG. 1A is an example architecture; the particular links between the feature detectors (104) may differ in various embodiments, which are not all depicted in the figures. A person of skill in the art may appreciate that such embodiments are contemplated herein. As an example, FIG. 1C and FIG. 1D show example MPNNs having one layer (102) of feature detectors (104).

Each layer (102, 102', 102") of feature detectors may comprise the structured determination of the output of the feature detectors (104), and each feature detector (104) may implement a computation that maps an input to an output.

The feature detectors (104) in a layer may accept a plurality of inputs from previous layers, combine them with a subset of weights, or parameters, W, and apply activation functions. Generally, the output of a feature detector in layer l may be provided as input to one or more feature detectors in layers l+1, l+2, . . . , L, where L is the number of layers of feature detectors. For example, in FIG. 1A, outputs of feature detectors (104) of layer (102) may be provided as input to one or more feature detectors (104) of a plurality of subsequent layers (102' and 102").

One or more feature detectors (104) may be implemented by processing hardware, such as a single or multi-core processor and/or graphics processing unit(s) (GPU(s)). Further, it will be understood that each feature detector (104) may be considered to be associated with an intermediate computation or an input of the neural network for an intermediate layer or an input layer, respectively. The use of large (e.g., with many intermediate computations) and deep (e.g., with multiple layers of computations) neural networks may improve the predictive performances of the MPNN compared to other systems.

As described elsewhere herein, the systems and methods described herein may use the MPNN to determine the molecular phenotypes of one or more pairs of biologically related variants, wherein the two variants in each pair may be referred to as variant t and variant r. The two corresponding molecular phenotypes may be denoted $m^t$ and $m^r$ respectively. It may be advantageous for the system 100 to comprise a further MPNN (101'), wherein the further MPNN is identically trained and configured as the first MPNN (101). This may be the case, for example, where the cost of obtaining processors is low, the desire for increased speed is high, and/or it is advantageous to perform variant analysis on the test variant and reference variant simultaneously. Alternatively, a single MPNN may be provided and the variants analysed one after the other, with the output of the first analysis being buffered at buffer (109) until the output of the second analysis is available.

The two molecular phenotypes $m^t$ and $m^r$ may be analyzed using a comparator (108), which determines the link distance for the two variants, $d^{tr}$. It will be appreciated that when processing links between one variant and multiple other biologically related variants, the molecular phenotype of the one variant may be determined by one application of the MPNN, stored, and then fed into the comparator along with the molecular phenotype for every one of the multiple other biologically related variants. It will also be appreciated that when processing links between variants in a first set of variants and variants in a second set of variants, all of the molecular phenotypes of the variants in the first and second set of variants may be determined by applying the MPNN and then stored at buffer (109), and then the comparator may be applied to every pair of variants consisting of one variant from the first set of variants and one variant from the second set of variants.

Returning now to the MPNN (101 and 101'), MPNN can operate in two modes: the forward-propagation mode and the back-propagation mode. In the forward-propagation mode, the MPNN may take as input X, apply a series of computations resulting in intermediate values Z, and then apply computations to ascertain the output Y. The quantities X, Y and Z may each be a scalar value, a vector of values, or a set of values. The MPNN may be configurable, and its configuration may be represented by parameters $W=(w_1, . . . , w_p)$, where p is the number of parameters. For any choice of configuration W, the output Y ascertained by the MPNN may be denoted by Y=F(X; where F defines the architecture of the MPNN.

Figure 1E:
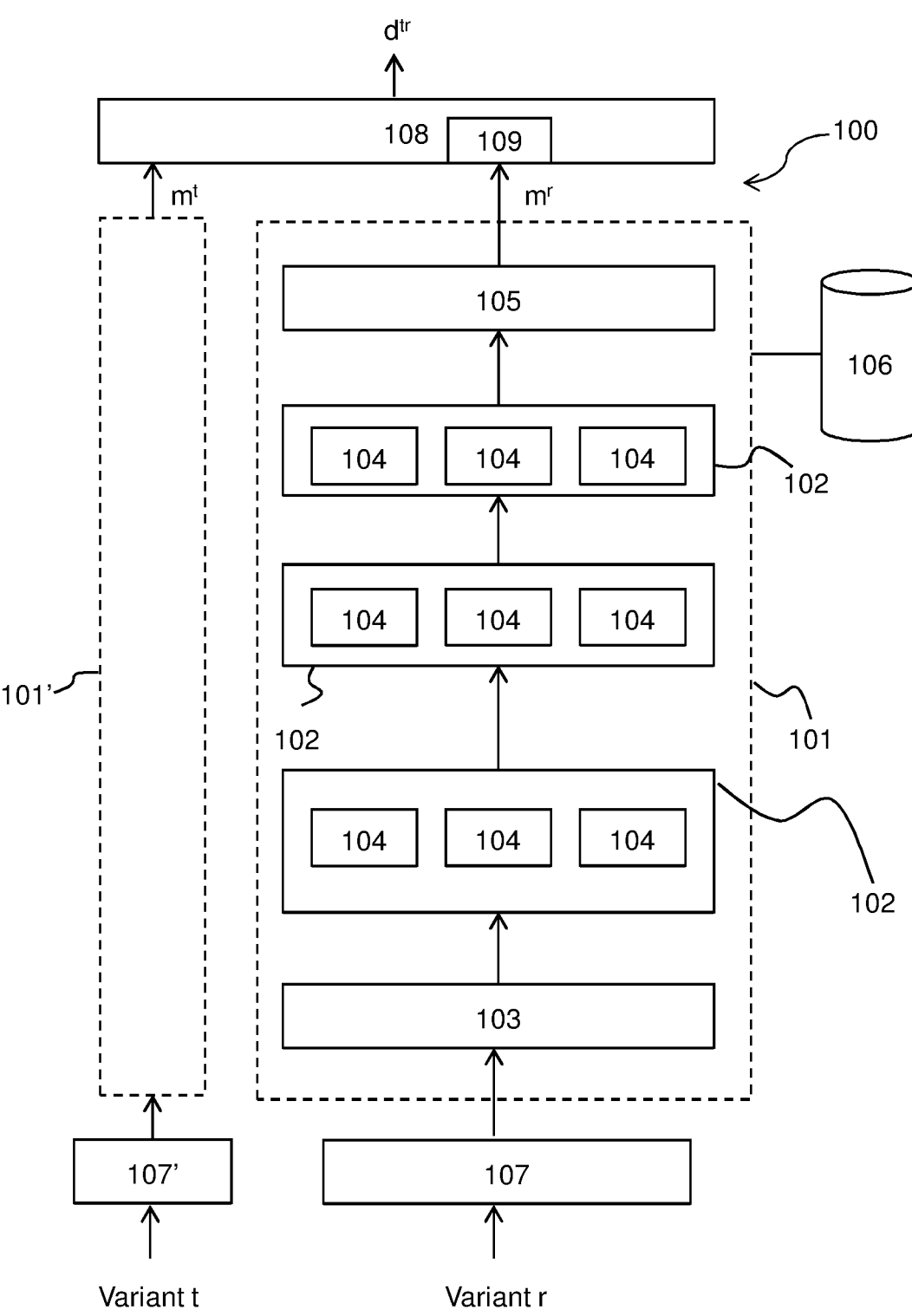
FIG. 1E is a block diagram illustrating a fifth embodiment of a system for linking biological sequence variants.

As shown in the system depicted in FIG. 1A, an MPNN may take as input a biological sequence and may also take as input a specification of the context. It may then apply a structured series of computations and output a numerical description of the molecular phenotype, which may comprise one or more numerical values or other information. The specification of the context may encode, for example, cell types, pairs of cell types, tissue types, age, sex, known biomarkers, patterns of behavior, blood chemistry, or other environmental factors. It may also encode sequence context, such as the chromosome, gene, or exon from which the input biological sequence was obtained. As shown in the system depicted in FIG. 1E, on the other hand, the MPNN may not take as input a context. The MPNN may be configurable, and its configuration may be determined by a set of parameters using machine learning training. The MPNN can be applied to a set of biologically related variants to determine the corresponding variant molecular phenotypes.

MPNNs can be used to evaluate a variety of molecular phenotypes. In one example, an MPNN may take as input a sequence of 600 nucleotides centered at the 3 prime splice site of exon 6 in the BRCA1 gene and a specification of tissue type, and output the percentage of BRCA1 transcripts in that tissue type that include exon 6.

Examples of molecular phenotypes that may be predicted using MPNNs include exon inclusion levels/percentages, alternative splice site selection probabilities/percentages, alternative polyadenylation site selection probabilities/percentages for a transcript, affinity of an RNA-protein or DNA-protein interaction, RNA- or DNA-binding protein specificities, microRNA specificities, specificity of microRNA-RNA interaction, the level of protein phosphorylation, phosphorylation patterns, the distribution of proteins along a strand of DNA containing a gene, the number of copies of a gene (transcripts) in a cell, the distribution of proteins along the transcript, and the number of proteins.

The system (100) may further comprise an encoder (107) functionally coupled to the input layer of the MPNN so that biological sequences, which are discrete-symbol sequences, can be encoded numerically and used as inputs to the MPNN. The encoder may further encode the context to be input to the MPNN. It may be advantageous for the system 100 to comprise a further encoder (107'), wherein the further encoder is identical to the first encoder (107). This may be the case, for example, where the cost of obtaining processors is low, the desire for increased speed is high and/or it is advantageous to perform variant analysis on the test variant and reference variant simultaneously. Alternatively, a single encoder may be provided and the biological sequence and the context may be encoded one after the other, with the output of the first analysis being buffered at buffer (110) until the output of the second analysis is available. It will be appreciated that the encoder may be applied in different ways and that an encoder may not be used at all, as depicted in FIG. 1B and FIG. 1D.

The encoder may, for example, encode the sequence of symbols in a sequence of numerical vectors (a vector sequence) using one-hot encoding. Suppose the symbols in the sequence come from an alphabet $\mathcal{A} =(\alpha_1, . . . , \alpha_k)$ where there are k symbols. The symbol $s_1$ at position i in the sequence is encoded into a numerical vector $x_i$ of length k: $x_i=(x_{i,1}, . . . , x_{i,k})$ where $x_{i,j}=[s_i=\alpha_j]$ and [•] is defined such that [True]=1 and [False]=0 (so called Iverson's notation). One-hot encoding of all of the biological sequence elements produces an m×r matrix X. For example, a DNA sequence CAAGTTT of length n=7 and with an alphabet $\mathcal{A}$ =(A, C, G, T), such that k=4, may produce the following vector sequence:

$$X = \begin{pmatrix} 0 & 1 & 1 & 0 & 0 & 0 & 0 \\ 1 & 0 & 0 & 0 & 0 & 0 & 0 \\ 0 & 0 & 0 & 1 & 0 & 0 & 0 \\ 0 & 0 & 0 & 0 & 1 & 1 & 1 \end{pmatrix}.$$

Such an encoding is useful for representing biological sequences as numeric inputs to the neural network. It will be appreciated that other encodings of X may be computed from linear or non-linear transformations of a one-hot encoding, so long as the transformed values are still distinct, or that other encodings may be used.

The MPNN also takes as input a specification of context, which may be numerical, categorical or an additional sequence. The specification of context may also in part be encoded by the encoder using, for example, a one-hot encoding scheme.

It is useful to compare the output of a MPNN Y to a desired output or target, Y'. The molecular phenotype target may be ascertained using experimental techniques, such as RNA-Seq, ChIP-Seq, microarrays, RT-PCR, SELEX, and massively parallel reporter assays. This is useful for training, in which the MPNN is configured using the parameters W such that, for input-target pairs (X, Y') in the training set of many such input-target pairs, the MPNN's output Y=F(X; W) is a good approximation of the training target Y', across the input-output pairs in the training set. The error or cost between the MPNN output Y and a target Y' can be quantified by, for example, the squared error $(Y-Y')^2$. It will be appreciated that different error or cost functions may be used. The error term is incorporated into a loss function L(X, Y'; W), which measures the discrepancy between the output of the MPNN and the desired output. In the example, L(X, Y'; W)=$(F(X; W)-Y')^2$. The process of training involves configuring W so as to minimize the total loss in a training set, such as the sum over the training examples of the loss for each example. Training may consist of determining a configuration W that minimizes or approximately minimizes the expected value or sum of L for pairs (X, Y') sampled from either training set or from a held-out validation set.

Alternatively or additionally, the MPNN may be operated in the back-propagation mode, which is used to determine how changes in the intermediate computations, the inputs, and the parameters may impact the output of the MPNN. These three types of changes are called gradients or derivatives and are denoted ∂Y/∂Z, ∂Y/∂X and ∂Y/∂W respectively. Note that while Z is not explicit in the input-output relationship Y=F(X; W), the output depends on the intermediate computations and so the gradient of the output with respect to the values produced by the intermediate computations can be determined. These gradients are useful for training.

An MPNN operating in back-propagation mode is a structured architecture that comprises a series of computations in a structured framework. First, the MPNN is operated in the forward-propagation mode to compute Y=F(X; W). Then, the MPNN is operated in the back-propagation mode, which comprises a series of computations that starts with the output of the MPNN and works its way back to the input, so as to determine the gradients ∂Y/∂Z, ∂Y/∂X and ∂Y/∂W for values produced by all of the intermediate computations Z, for all inputs X, and for all parameters W.

MPNNs are configured by training their parameters using one or more neural network training procedures applied to a training dataset. The dataset consists of examples of biological sequences, specifications of context, and corresponding molecular phenotypes. An important aspect of MPNNs is their ability to generalize to new conditions, that is, to biological sequences and contexts that are not in the training dataset. This aspect enables MPNNs to determine the molecular phenotypes of variants that are not in the training dataset or to variant-context combinations that are not in the training dataset.

In one example, an MPNN takes as input a subsequence of length 600 nucleotides centered at the 3 prime end of exon 6 in BRCA1 (a splice site region variant), and a one-hot encoding of the cell type, and through a structured series of computations determines the percentage of BRCA1 transcripts that include exon 6. This MPNN may have been trained using BRCA1 exon 6 splice region variants and corresponding measurements of splicing percentages, obtained by DNA and RNA sequencing of patients. This MPNN can be used to analyze BRCA1 exon 6 splice site region variants. It can also be used to analyze splice site region variants from other exons in BRCA1 and even for other exons in other genes, but it may not be accurate in these cases because it was trained using only data for exon 6 in BRCA1.

In another example, an MPNN takes as input a subsequence of length 600 nucleotides centered at the 3 prime end of any exon in the human genome, and a one-hot encoding of the cell type, and through a structured series of computations determines the percentage of transcripts that include the exon, out of all those transcripts generated from the gene containing the exon. This MPNN may have been trained using splice region variants from chromosomes 1 to 10 and corresponding measurements of splicing percentages, obtained by DNA and RNA sequencing of a single healthy individual. This MPNN can be used to analyze BRCA1 exon 6 splice site region variants, but it can also be used to analyze splice site region variants from other exons in BRCA1 and for other exons in other genes. Even though it was trained using data for chromosomes 1 to 10, it may generalize well to the other chromosomes.

In another example, an MPNN takes as input a subsequence of length 600 nucleotides centered at the 3 prime end of any exon in the human genome, and a one-hot encoding of the cell type, and a one-hot encoding of the gene in which the exon is located, and through a structured series of computations determines the percentage of transcripts that include the exon, out of all those transcripts generated from the gene containing the exon. By providing the gene identity as input to the MPNN, the MPNN may account for gene-specific effects on the molecular phenotype, as well as for gene-independent effects.

The MPNN examples described above may each be implemented by the same or possibly different MPNN structures; that is, the number, composition and parameters of the nodes and layers may or may not differ. It will be appreciated that the biological sequences need not be of the same length and that an MPNN may be trained to account for other molecular phenotypes, for other biologically related variants, and/or for other specifications of context.

The MPNN may be configured in different ways such as to use a discriminative neural network, a convolutional neural network, an autoencoder, a multi-task neural network, a recurrent neural network, a long short-term memory neural network, or a combination thereof. It will also be appreciated that many different machine learning architectures can be represented as neural networks, including linear regression, logistic regression, softmax regression, decision trees, random forests, support vector machines and ensemble models. Differences between techniques and architectures often pertain to differences in the cost functions and optimization procedures used to configure the architecture using a training set.

It will also be appreciated that the MPNN may also take as input a vector of features that are derived from the variant sequence. Examples of features include locations of protein binding sites, RNA secondary structures, chromatin interactions, and protein structure information.

It will be appreciated that the MPNN may be applied to a set of variants to determine the molecular phenotypes of the variants in the set of variants.

Since biologically related variants may be derivable from a reference sequence, in another embodiment, the MPNN is used to determine the molecular phenotype of a variant as it relates to the molecular phenotype of the reference sequence. For example, consider an MPNN that is configured to determine the percentage of transcripts that include exon 6 of BRCA1 using the 600 nucleotide sequence centered at the 3 prime end of the exon. The MPNN may be applied to the reference sequence extracted from the reference genome, and also to the variants from the patient. The percentage value for the reference genome may be subtracted from the percentage values for the patients, resulting in variant molecular phenotypes that measure the change in the percentage. It will be appreciated that the comparison of the variant and the reference sequence may be performed in different ways, including using the difference, the absolute difference, and the squared difference. For multi-valued molecular phenotypes, the sum of the differences, the sum of the absolute differences and the sum of the squared differences may be used. For probability distributions, Kullback-Leibler divergence may be used. For example, if the output of the MPNN is a probability distribution over a discrete variable, the variant molecular phenotype may be computed using the Kullback-Leibler divergence between the probability distribution ascertained from the variant and the reference sequence. It will be appreciated that more than one reference sequence may be used and the comparison may be adjusted accordingly, such as by determining the maximum or the average of the differences between the outputs for the variant and the references. It will be appreciated that the one or more reference sequences may be obtained in different ways, such as by sequencing the DNA from one or more close relatives of the patient; by examining the reference genome, the reference transcriptome or the reference proteome; by sequencing a gene using a sample from a patient's tumour; or by sequencing the gene using a sample from an unaffected tissue in the same patient.

The methods and systems described herein can be used to analyze variants in different contexts. For instance, when a child's variant is compared to a reference sequence obtained from the reference human genome, the MPNN may produce a large variant-induced molecular phenotype, indicating that the variant may be disease causing. But, when the same variant is compared to the reference sequences obtained from his or her unaffected parents, the MPNN may produce a low variant-induced molecular phenotype, indicating that the variant may not be disease causing. In contrast, if the MPNN produces a large variant-induced molecular phenotype when the parents' sequences are used as the reference, then the variant is more likely to be the cause of the disease.

Another circumstance in which different reference sequences arise is when the variant may be present in more than one transcript, requiring that the impact of the variant be ascertained in a transcript-dependent fashion. Also, since the MPNN may take as input a description of the environment, such as a one-hot encoding of the cell type, the variant-induced molecular phenotype can depend on the context as established by the environment. A variant may, for example, not induce a molecular phenotype in a liver cell, but induce a large molecular phenotype in a brain cell.

Figure 12:
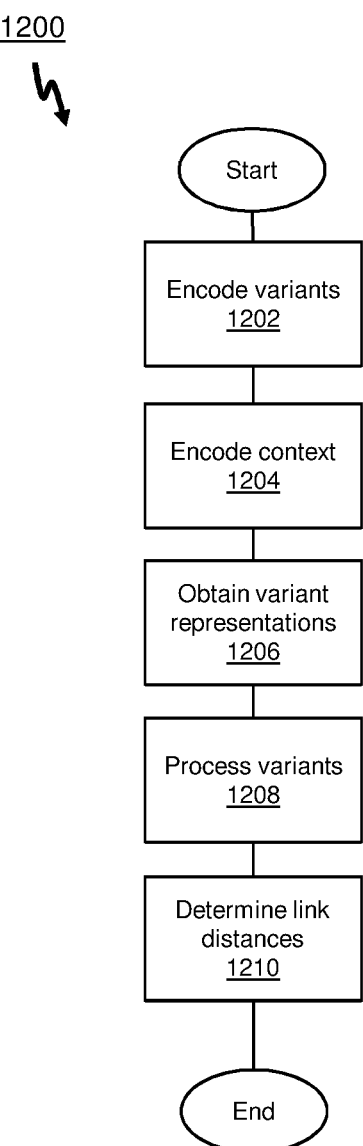
FIG. 12 is a flowchart showing a method for linking biological sequence variants.

FIG. 12 illustrates a flowchart that summarizes the above steps performed by system 100. A method (1200) for linking two or more biologically related variants derived from biological sequences comprises: at block 1202, each of two or more digital representations of the two or more biologically related variants may be generated by the encoder; at block 1204, digital representations of the one or more contexts may be generated by the encoder; at block 1206, obtaining at an input layer of a molecular phenotype neural network (MPNN), each of the two or more digital representations of the two or more biologically related variants, each comprising one or more input values digitally representing a variant and, possibly, the one or more contexts; at block 1208, processing each variant by the MPNN, the MPNN comprising one or more feature detectors configured to obtain input from at least one of: (i) the one or more of the input values of the respective variant and (ii) an output of a previous feature detector, the MPNN configured to provide output values representing a molecular phenotype for the variant, comprising one or more numerical elements of one or more of the feature detectors; at block 1210, for each of one or more pairs of variants in the two or more biologically related variants, determining, by a comparator, a numerical link distance comprising comparing the molecular phenotypes for the pair of variants.

Figure 2:
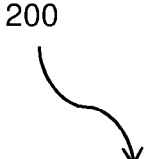
FIG. 2 is a block diagram illustrating a first example architecture of a molecular phenotype neural network.
Figure 2:
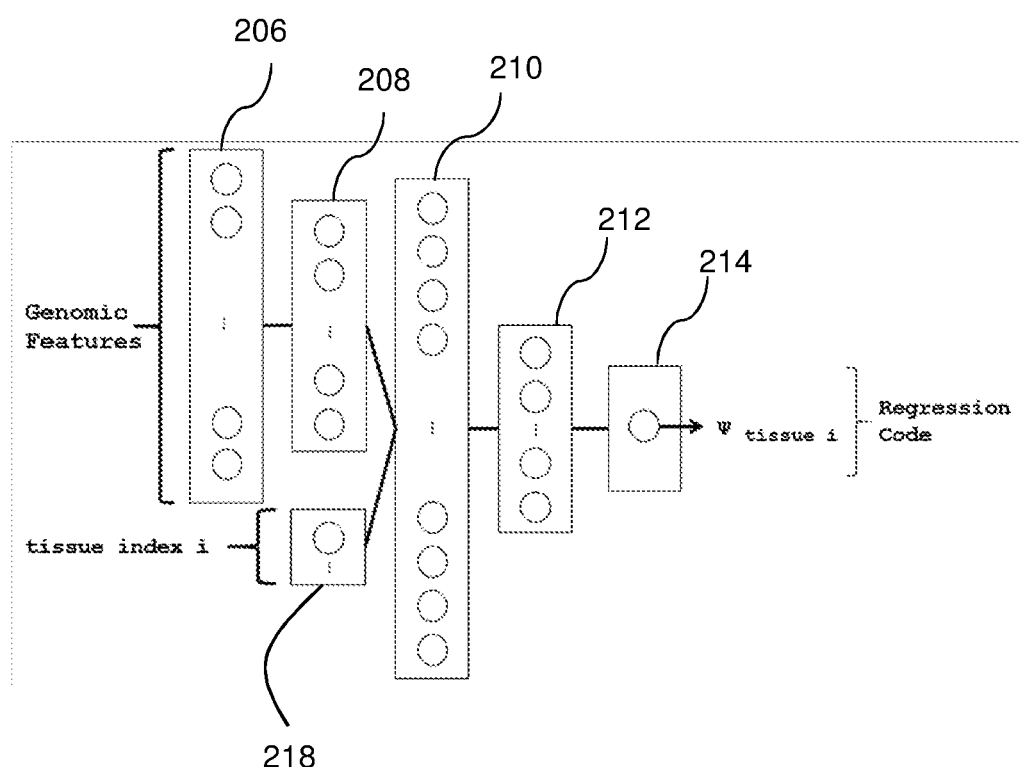

Referring now to FIG. 2, shown therein is an example architecture (200) of an MPNN that has a layer of input values that represent genomic features (206) that are DNA sequences, encoded DNA sequences, or other features derived from DNA sequences, wherein the DNA sequences containing an exon, the neighbouring introns and the neighbouring exons as well as the annotated splice junctions. The layer of input values also includes a specification of the context in the form of the tissue index (218). In this example, where are three layers of feature detectors (208, 210 and 212). In this example, using these layers of feature detectors, the MPNN processes the inputs through three layers of feature detectors (208, 210, 212) that apply a structured series of computations to determine an output (214), which in this example is the percentage of transcripts that include the exon $\Psi$, at the output layer. This MPNN may be viewed as a regression model. The input values representing genomic features comprise input to the first layer of feature detectors (208). In this example, the input values representing the tissue index (218) and the outputs of the feature detector from the first layer of feature detectors (208) comprise the inputs to the second layer of feature detectors (210). The outputs of the second layer of feature detectors (210) comprise the inputs to the third and final layer of feature detectors (212). The outputs of the third and final layer of feature detectors (212) are the molecular phenotype values (214). It will be appreciated that different architectures may be used. For example, the input values representing the tissue index (218) may be inputs to the first layer of feature detectors (208) and the first layer of feature detectors may be the final layer of feature detectors and the outputs of the first layer of feature detectors may be the molecular phenotype values (214). For example, there may be more than three layers of feature detectors. The values in the input layer may be inputs to the second and third layers of feature detectors. It will be appreciated that values in the input layer may be derived in different ways or encoded in different ways. For example, the values in the input layer (206) may include binding specificities of RNA- and DNA-binding proteins, RNA secondary structures, nucleosome positions, position-specific frequencies of short nucleotide sequences, and many others. The context (e.g., tissue index) may also be derived or encoded in different ways, such as by using an encoder (not shown), which encodes the tissue index i using a 1-of-TT binary vector where TT represents the number of conditions and the values in the vector are zero everywhere except at the position indicating the condition, where the value is one. This is called one-hot encoding.

Figure 3:
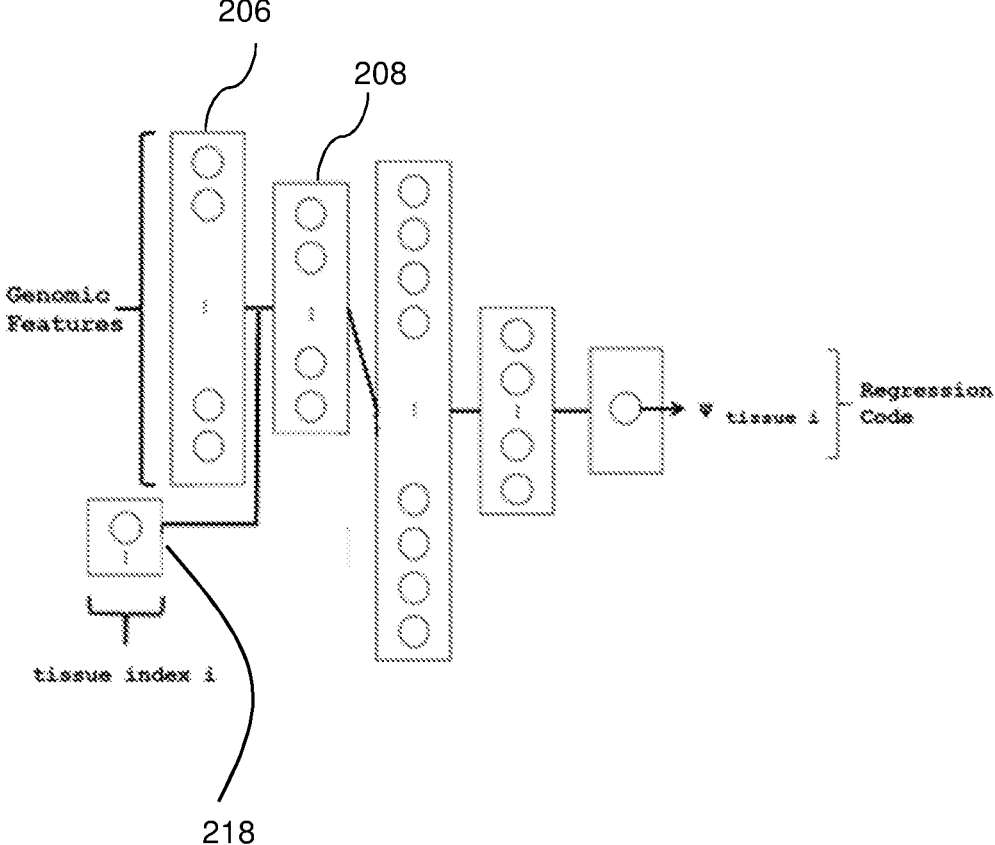
FIG. 3 is a block diagram illustrating a second example architecture of a molecular phenotype neural network.

FIG. 3 shows another example where the input values representing context (204) along with the input values representing genomic features comprise inputs to the first layer of feature detectors (208).

Figure 4:
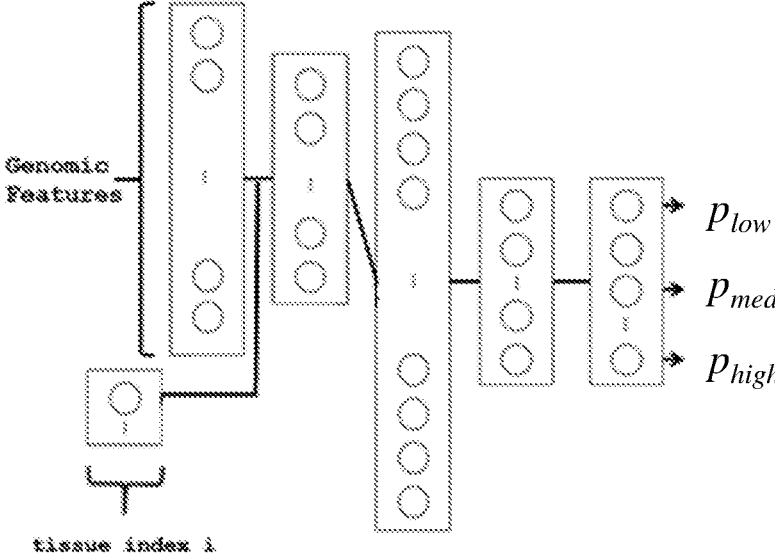
FIG. 4 is a block diagram illustrating a third example architecture of a molecular phenotype neural network.

Referring now to FIG. 4, it will be appreciated that the molecular phenotype may be represented in different ways. Instead of determining a real-valued Ψ in the form of a percentage, the MPNN may output probabilities over discrete molecular phenotype categories. For example, the percentage may be binned into low (between 0 and 33%), medium (34% to 66%), and high (67% to 100%) categories, and the output of the MPNN may be three real numbers between zero and one that add up to one: $P_{low}$, $P_{med}$, $P_{high}$. The molecular phenotype targets for training this MPNN may be one-hot encoded vectors, (1,0,0), (0,1,0), and (0,0,1), or probability distributions that take into account measurement noise. For these discretized molecular phenotype values, the cross entropy cost function or the log-likelihood performance measure can be used for training.

Figure 5:
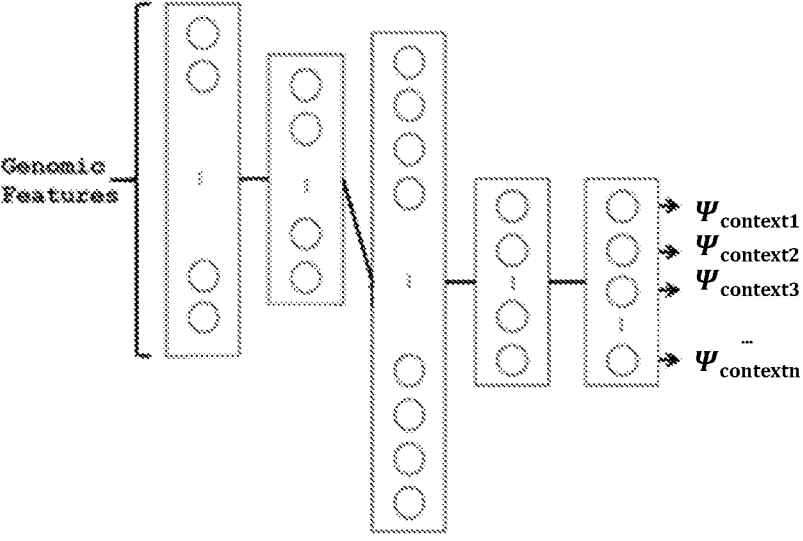
FIG. 5 is a block diagram illustrating a fourth example architecture of a molecular phenotype neural network.
Figure 6:
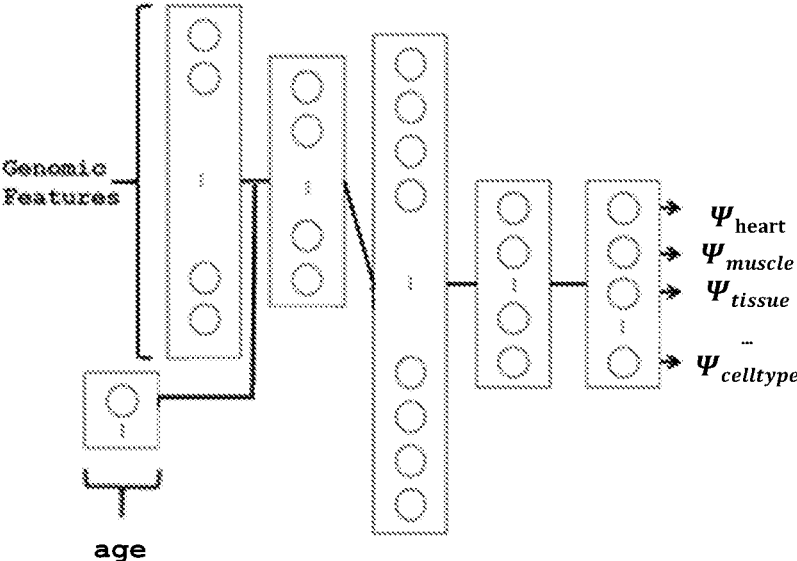
FIG. 6 is a block diagram illustrating a fifth example architecture of a molecular phenotype neural network.

Referring now to FIG. 5, it will be appreciated that instead of encoding the context as an input to the MPNN, the MPNN may output a different molecular phenotype value for each context. Here, the MPNN determines the percentage of transcripts that include the exon for every one of the T tissue types. These T numerical values together comprise the molecular phenotype. It will be appreciated that hybrid approaches are possible, where part of the context is provided as input and the molecular phenotype is provided for every other aspect of the context. Referring now to FIG. 6, for example, the age of the patient may be provided as an input to the MPNN, and the MPNN may provide a molecular phenotype value for each of T different tissue types, such as heart, muscle, tissue, etc.

Referring back to FIG. 1A, in the training phase, the MPNN (101) can be configured by adjusting its parameters using a dataset of biological sequences, specifications of context, and corresponding molecular phenotypes. This comprises establishing an MPNN and then repeatedly updating the one or more parameters, or weights, of the MPNN so as to decrease the error between the molecular phenotypes determined using the MPNN and the measured molecular phenotypes, until a condition for convergence is met at which point the parameters are no longer updated. It will be appreciated that instead of decreasing the error, the objective may be to decrease another loss function such as cross entropy, or to maximize an objective function, such as log-likelihood. The resulting parameters, or weights, are then stored in the memory (106) such that the MPNN parameters can be reused during application to analyze variants. At each step of the updating of one or more parameters, the entire batch of data may be used, or a subset of examples called a minibatch may be used, the examples in the minibatch being selected randomly or by using a predetermined pattern.

Referring again to FIG. 1A, embodiments comprising a comparator (108) can be used to link variants by using MPNNs to determine the variant molecular phenotypes and then, for any two variants, determining a link distance by comparing their molecular phenotypes. These link distances are used to identify, score, prioritize, or rank the variants. Knowledge about one variant can be associated with another variant by examining the link distance. Knowledge may include English language descriptions, interpretations and mechanistic explanations; functional annotations; and/or literature references.

For two variants, the comparator may determine the link distance as a numerical value indicating the strength of the link between the two variants, where a strong link has a low link distance and a weak link has a high link distance. The link distances between a test variant and multiple established variants can further be compared to identify which established variants are most strongly linked to the test variant.

In conjunction with link distances, the term "prioritization," as used herein, generally refers to the process of producing a sorted list of variants to identify the order in which variants may be examined, processed, classified, or otherwise considered for further analysis.

In one embodiment, for one or more pairs of biologically related variants, the MPNN is used to determine the variant molecular phenotype for every variant. The comparator determines link distance between the variants in each pair by summing the output of a nonlinear function applied to the difference between the molecular phenotypes for the two variants. The nonlinear function may be the square operation. The nonlinear function may be the absolute operation.

In one embodiment, the link distance between a pair of variants t and r for context c is determined by first ascertaining their real-valued molecular phenotypes $m_c^t$ and $m_c^r$ using the MPNN. The context-specific link distance $d^{tr}$ between the two variants may be computed using one of the formulas:

$$d^{tr}=m_c^t-m_c^r, \quad d^{tr}=(m_c^t-m_c^r)^2, \quad d^{tr}=|m_c^t-m_c^r|,$$

where |•| is the absolute function. This may be repeated for all pairs of biologically related variants or for a subset of pairs. It will be appreciated that the MPNN may need be applied only once for each variant, and that the comparator (108) may apply various other computations to compute the link distance.

In another embodiment, the molecular phenotype determined using the MPNN is a vector of values, so that $m_{c,1}^t$, $m_{c,1}^t$, . . . , $m_{c,q}^t$) and $m_c^r=(m_{c,1}^r, m_{c,1}^r, . . . , m_{c,q}^r)$. The context-specific link distance between the two variants may be computed using one of the operations:

$$d^{tr} \leftarrow \Sigma_{n=1}^q (m_{c,n}^t - m_{c,n}^r), \quad d^{tr} \leftarrow \Sigma_{n=1}^q (m_{c,n}^t - m_{c,n}^r)^2,$$
$$d^{tr} \leftarrow \Sigma_{n=1}^q |m_{c,n}^t - m_{c,n}^r|,$$

where |•| is the absolute function. This may be repeated for all pairs of biologically related variants or for a subset of pairs. It will be appreciated that the MPNN may need be applied only once for each variant, and that the comparator (108) may apply various other computations to compute the link distance.

In another embodiment, the molecular phenotype is a vector of values corresponding to probabilities over different possible categories, the probabilities summing to one. The context-specific link distance between the two variants may be computed using an operation that accounts for probabilities in the fashion of the Kullback-Leibler divergence:

$$d^{tr} \leftarrow \Sigma_{n=1}^{q} m_{c,n}^{t} \log(m_{c,n}^{t}/m_{c,n}^{r}), d^{tr} \leftarrow \Sigma_{n=1}^{q} m_{c,n}^{r} \log(m_{c,n}^{r}/m_{c,n}^{t}),$$

In another embodiment, the molecular phenotypes for every context c=1 . . . T is determined using the MPNN, and they are placed in a vector for each pair of variants: $m^t = (m_1^t, \ldots, m_T^t)$ and $m^r = (m_1^r, \ldots, m_T^r)$ where T is the number of contexts. The link distance between the two variants may be computed using one of the formulas:

$$d^{tr} \leftarrow \Sigma_{c=1}^{T}(m_c^t - m_c^r), d^{tr} \leftarrow \Sigma_{c=1}^{T}(m_c^t - m_c^r)^2,$$
$$d^{tr} \leftarrow \Sigma_{c=1}^{T}|m_c^t - m_c^r|.$$

When summing across contexts, predetermined numerical scaling factors may be used to give higher weight to some conditions compared to others. For example, denoting the set of scale factors for the different conditions by $\alpha_1, \ldots, \alpha_T$, one of the following formulas may be used to compute the link distance:

$$d^{tr} \leftarrow \Sigma_{c=1}^{T} \alpha_c (m_c^t - m_c^r), d^{tr} \leftarrow \Sigma_{c=1}^{T} \alpha_c (m_c^t - m_c^r)^2,$$
$$d^{tr} \leftarrow \Sigma_{c=1}^{T} \alpha_c |m_c^t - m_c^r|.$$

This may be repeated for all pairs of biologically related variants or for a subset of pairs. It will be appreciated that the MPNN may need be applied only once for each variant. It will be appreciated that the comparator may apply various other computations to compute the link distance.

It will be appreciated that this method can be applied using MPNNs that compute several different molecular phenotypes and these may be combined to determine link distances. It will be appreciated that multiple MPNNs may be applied to compute multiple molecular phenotypes and these may be combined to determine link distances. It will be appreciated that multiple MPNNs may be applied to compute multiple link distances and that these may be combined to determine link distances.

Figure 11:
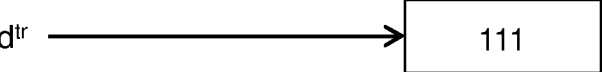
FIG. 11 is a block diagram showing a labeling unit.

In another aspect, for a set of biologically related variants wherein some of the variants are labeled, the MPNN-determined link distances between the other variants and the labeled variants can be used to associate the labels with the other variants. The label of one of the other variants may be determined by computing the link distances of the other variant to one or more of the labeled variants. The label of the other variant may be determined from the label of the labelled variant that has the lowest link distance. Alternatively, the label of the other variant may be determined by computing the weighted average of the labels of the labelled variants, where the weights are nonlinear functions of the link distances. Two or more other variants may be prioritized, by sorting them according to their label values. Two or more other variants may be partially sorted according to their label values, that is, the k other variants with smallest link distance may be identified and sorted, where k is smaller than the number of other variants. The determined label may be applied to the variant by the labeling unit (111), as shown in FIG. 11.

To illustrate, suppose the system determines that a test variant causes a change in a particular molecular phenotype, say the splicing level of a specific exon. Suppose a nearby, labelled variant whose disease function is well characterized causes a similar change in the exact same molecular phenotype. Since variants act by changing cellular chemistry, such as the splicing level of the exon, it can be inferred that the test variant likely has the same functional impact as the labelled variant. The system can ascertain the link distance between the two variants in this fashion using a variety of different measures. Because the MPNN can take a specification of context, such as cell type, as input, this information can be used to more accurately associate variants with one another. For example, two variants that have similar molecular phenotypes in brain tissue may be associated more strongly than two variants that have similar molecular phenotypes, but in different tissues.

One class of labels may measure deleteriousness. A "deleteriousness label," as used herein, generally refers to a classification, category, level, or numerical value that is associated with a variant and that relates its level of deleteriousness for one or more functions or categories. It may be derived using evolutionary analysis, an analysis of how severely the variant damages a biological process or biomolecule, knowledge about the variant's disease function, or other information pertaining to the variant. A deleteriousness label may contain a set of numerical values that each indicates the degree of deleteriousness in one of multiple categories of deleteriousness. It will be appreciated that deleteriousness has a broad definition and that the methods and systems described herein may be applied to deleteriousness labels, but also to labels of related or other kinds.

More generally, labels may represent additional information that may be associated between variants of similar function. Labels may be categorical, with two values, such as "yes" and "no," or "damaging" and "non-damaging," or may have one of more than two values, such as "benign," "likely benign," "likely pathogenic," "pathogenic," and "uncertain significance." Labels may real-valued, such as a real number between zero and one, where zero corresponds to low pathogenicity and one corresponds to high pathogenicity. Labels may be scores with numeric values that indicate how deleterious, pathogenic, or damaging variants are expected to be. The labels may reflect other quantitative aspects of gross phenotype, phenotype or molecular phenotype, such as those associated with diabetes, cardiovascular conditions and neurological disorders. An example is the IQ coefficient. Labels may be vector-valued; for example, three quantitative phenotypes can be encoded as a vector of length 3, (value 1, value 2, value 3). Categorical labels may be encoded as vectors using one-hot encoding. For example, the categories "benign", "likely benign", "likely pathogenic" and "pathogenic" can be encoded as the vector labels (1,0,0,0), (0,1,0,0), (0,0,1,0) and (0,0,0,1). It will be appreciated that labels may be encoded in different ways and that the systems and methods described herein can be applied.

Figure 7:
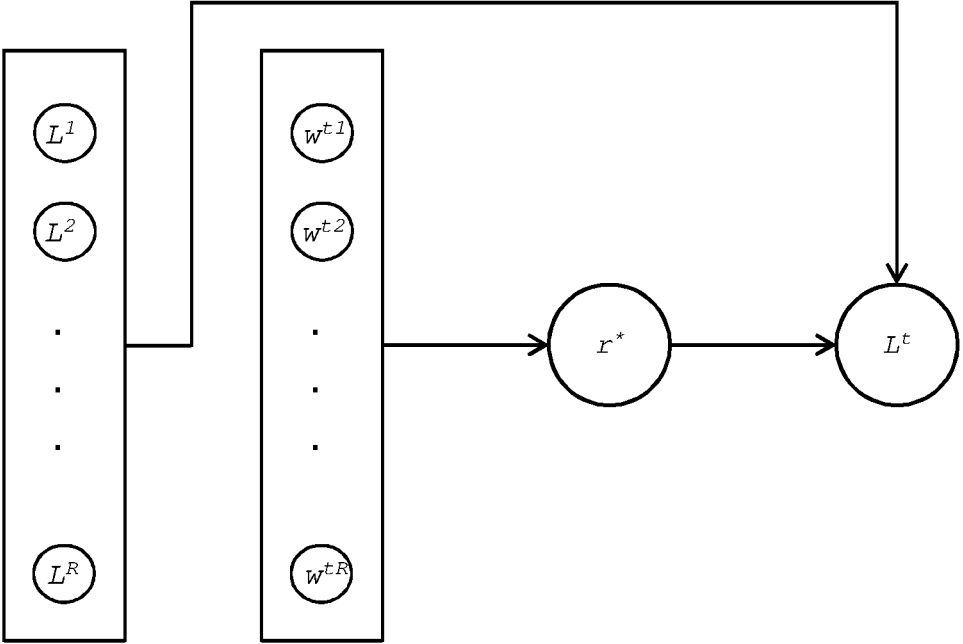
FIG. 7 is a block diagram illustrating labeling of variants.

Referring now to FIG. 7, labels for deleteriousness may be associated with some variants and these labeled variants may be used to determine labels for other variants. For example, denoting the label for variant r by $L^r$, the label may be a one-hot encoding of a classification, such as where a label of (1,0) indicates that the variant is not deleterious and a label of (0,1) indicates that the variant is deleterious. The label may be real-valued, such as a real number between 0 and 1, where 0 indicates that the variant is not deleterious and 1 indicates that it is deleterious. It is appreciated that other categorical, numerical, or vector-numerical labels may be used. The labels of the other variants indexed by t may be determined using the labeled variant with lowest link distance, with the formula:

$$L^t \leftarrow L^{r^*}, \text{ where } r^* \text{ is selected such that } d^{tr^*} \leq d^{tr} \text{ for all labeled variants } r.$$

Figure 8:
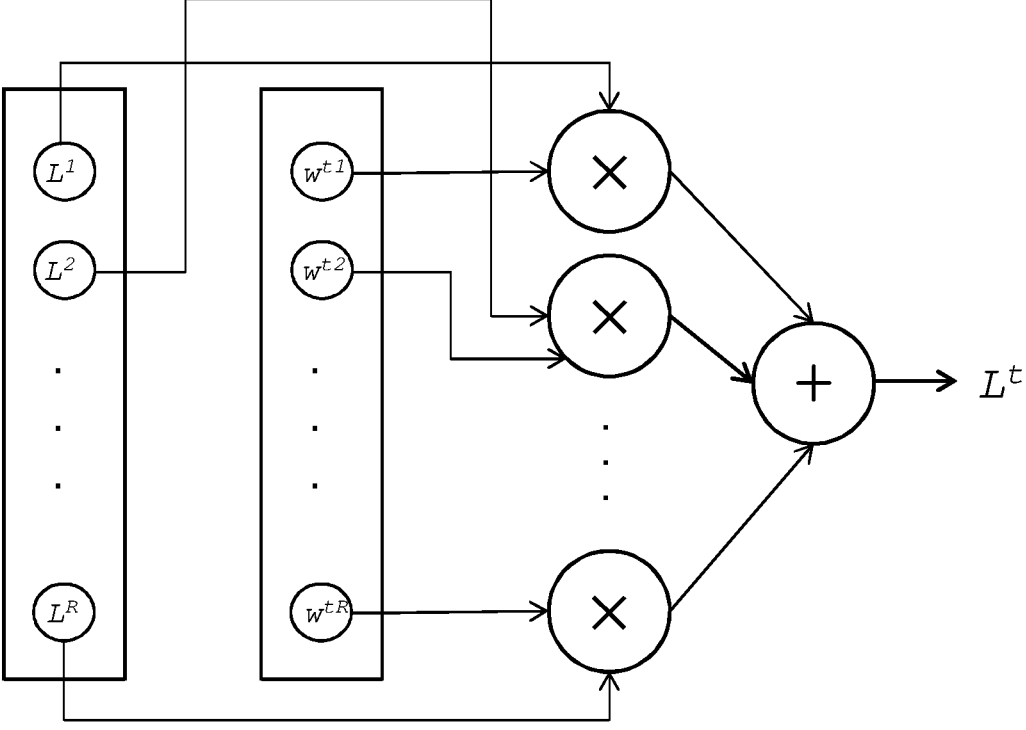
FIG. 8 is a block diagram illustrating weighting for labeling of variants.
Figure 9:
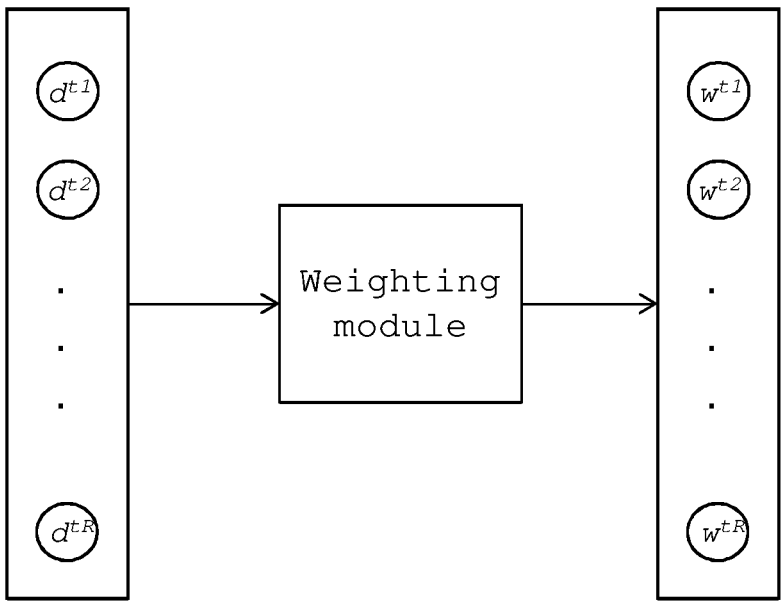
FIG. 9 is a block diagram illustrating the determination of weights used for weighting for labeling of variants.

Referring now to FIG. 8, the labels for the other variants may be determined by a weighted average of the labels of the labeled variants. Referring now to FIG. 9, for another variant t, a weighting module may be applied to determine the weights for all labeled variants and then the weights may be used to combine the labels of the labeled variants:

$$L^t \rightarrow \Sigma_{r=1}{}^R w^{tr} L^r.$$

This weighted combination of labels may require that the labels be represented numerically, such as using one-hot encoding. It will be appreciated that other numerical encodings of labels are possible and that the label may represent a continuous quantity, such as a probability distribution or a real-valued pathogenicity level.

Referring now to FIG. 9, the weighting module may take as input link distances and outputs a set of weights. For example, denoting the weight for the other variant t and the labeled variant r by $w^{tr}$, the weights are determined by applying a linear or a nonlinear weighting module to the link distances:

$$(w^{t1}, wt^2, \ldots, w^{tR}) \leftarrow f(d^{t1}, d^{t2}, \ldots, d^{tR}),$$

where f ( ) is the result of the linear or nonlinear weighting module and the labeled variants are indexed by $1, \ldots, R$.

The weighting module may determine the weights for different labeled variants independently:

$$(w^{t1}, w^{t2}, \ldots, w^{tR}) \leftarrow (f'(d^{t1}), f'(d^{t2}), \ldots f'(d^{tR}))$$

where f' ( ) is the result of the weighting module applied to each link distance individually. This corresponds to a weighting module with the following form:

$$f(d^{t1}, d^{t2}, \ldots, d^{tR}) = (f'(d^{t1}), f'(d^{t2}), \ldots f'(d^{tR})).$$

Examples of such weighting modules f' ( ) include:

$$f'(d^{tr}) \leftarrow 1/(1 + \alpha d^{tr}),$$

$$f'(d^{tr}) \leftarrow \exp(-\alpha d^{tr}),$$

$$f'(d^{tr}) \leftarrow 1/(1 + \exp(\alpha(d_0 - d^{tr}))),$$

where $\alpha$ and $d_0$ are predetermined numerical parameters. $\alpha$ determines how quickly the magnitude of the weight drops off when the link distance increases. The first two formulas may cause the weight to drop immediately when the link distance increases from zero. The third formula may allow for the weight to drop off only when it starts to approach a threshold on the link distance, $d_0$. It will be appreciated that other nonlinear weighting functions may be used.

Figure 10:
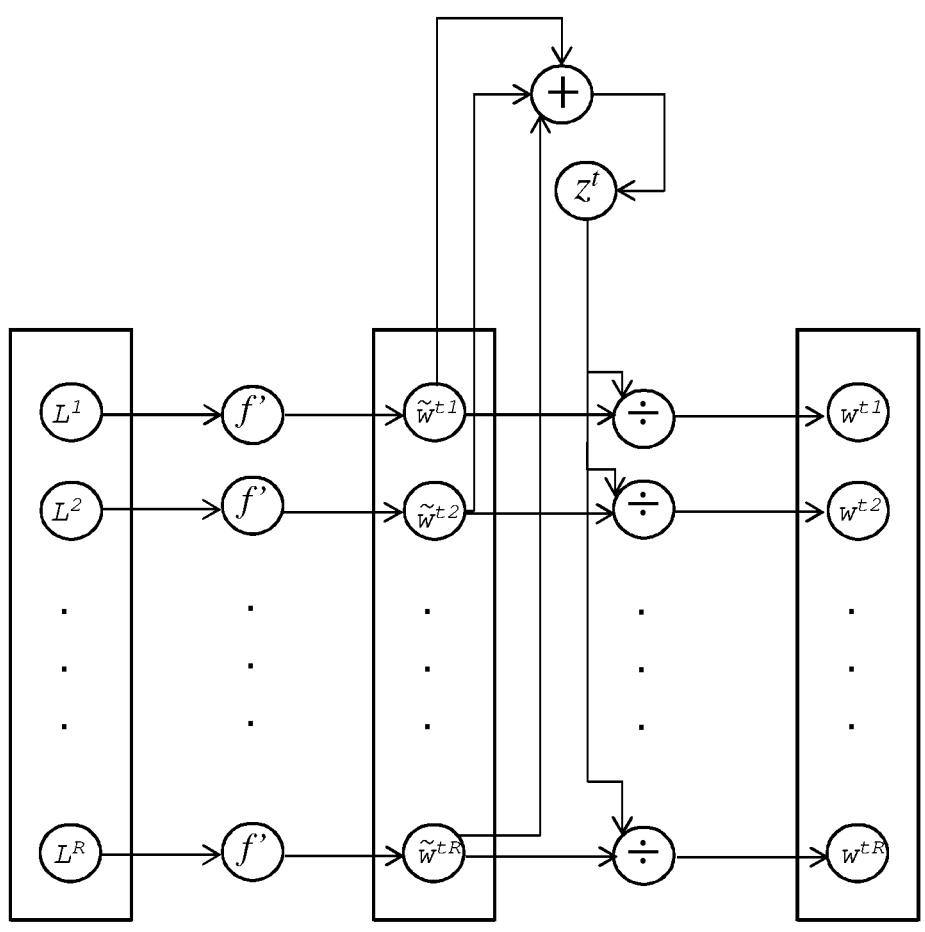
FIG. 10 is a second block diagram illustrating the determination of weights used for weighting for labeling of variants.

Referring now to FIG. 10, the weighting module may determine the weights for different labeled variants in a way that depends on more than one labeled variant. For example, the weights for one other variant and all labeled variants may be normalized so that the sum over the labeled variants is one. The weighting module may first compute the un-normalized weights independently for different labeled variants:

$$\tilde{w}^{tr} \leftarrow f'(d^{tr}), \text{ for } r=1, \ldots, R.$$

Then, the weighting module may determine the normalization factor:

$$z^t = \Sigma_{r=1}{}^R \tilde{w}^{tr}.$$

Lastly, the weighting module may output the normalized weights:

$$(w^{t1}, w^{t2}, \ldots, w^{tR}) \leftarrow (\tilde{w}^{t1}/z^t, \tilde{w}^{t2}/z^t, \ldots, \tilde{w}^{tR}/z^t)$$

It will be appreciated that these computations can be performed differently so as to achieve the same or a very similar effect.

Another example of a weighting module that determines the weights for different labeled variants in a way that depends on more than one labeled variant, is a weighting module that places all weight on the labeled variant with the lowest link distance. The weighting module may first identify the labeled variant with lowest link distance:

$$r^* \leftarrow \arg \min_r d^{tr},$$

Then, it may set the corresponding weight to one and the others to zero:

$$(w^{t1}, w^{t2}, \ldots, w^{tR}) \leftarrow ([r^*=1], [r^*=2], \ldots, [r^*=R]),$$

where [ ] indicates Iverson's notation, as described above. It will be appreciated that the set of weights may be determined efficiently by setting all weights to zero and then setting the weight for label r* to one.

After the weights are computed, the label of the other variant t may be determined by combining the labels of the labeled variants, using the weights:

$$L^t \leftarrow \Sigma_{r=1}{}^R w^{tr} L^r.$$

It will be appreciated that labeled variants that have a weight of zero need not be explicitly multiplied by their weights and summed over:

$$L^t \leftarrow \Sigma_{r \in \{1, \ldots, R\}, w^{tr} \neq 0} w^{tr} L^r.$$

In the case of picking the labeled variant with lowest link distance, this summation reduces to $$L^t \leftarrow L^{r^*}.$$

Another example of a weighting module that determines the weights for different labeled variants in a way that depends on more than one labeled variant, is a weighting module that outputs equal weights on the $\rho$ labeled variants that have lowest link distance.

The weighting module parameters, such as $\alpha$, $\rho$, $d_0$ may be set by hand or by searching over appropriate values using a dataset of variants with known labels, such as to obtain the highest possible correct label classification rate.

The labels may be encoded as real-valued or binary-valued vectors, in which case the weighted combination of labels may result in a vector label of the same length. If the reference variant labels use a one-hot encoding, such as one in which a label of (1,0) indicates that the variant is not deleterious and a label of (0,1) indicates that the variant is deleterious, the weighted combination of the labels of the labeled variants will result in a real-valued vector. For example, if the normalized weights for 5 labeled variants are 0.5, 0.3, 0.1, 0.1, 0.0 and the labeled variants have labels (0,1), (0,1), (1,0), (1,0), (1,0), then the label of the other variant may be $0.5 \times (0,1) + 0.3 \times (0,1) + 0.1 \times (1,0) + 0.1 \times (1,0) + 0.0 \times (1,0)$, which equals (0.2, 0.8), indicating that the label (0,1) has more evidence than the label (1.0), but that there is some uncertainty. It will be appreciated that this is a small example and that in practical applications the number of variants may be higher, such as in the thousands, in the millions or even higher.

Once the labels have been determined for a set of other variants indexed from 1 to $\tau$, the other variants may be prioritized by sorting their labels. If the labels use a one-hot encoding, such as one in which a label of (1,0) indicates that the variant is not deleterious and a label of (0,1) indicates that the variant is deleterious, the second label value for each other variant may be used for prioritization. For example, if there are 4 other variants with labels (0.2,0.8), (0.7,0.3), (0.1,0.9), (0.9,0.1) corresponding to other variants 1, 2, 3 and 4, and the second label value, which corresponds to the deleterious label, is used, the 4 other variants may be prioritized using the values 0.8, 0.3, 0.9, and 0.1. Sorting this list of values may yield a prioritized list of other variants: 3, 1, 2, 4, that is, other variant 3 is the "most deleterious" and other variant 4 is the "least deleterious." The other variants prioritized in this way may be subject to subsequent analysis, which may include further computational analysis or experimental analysis. It will be appreciated that the other variants may be prioritized in different ways using the labels.

The weights used to combine the labels of the labelled variants can be constructed so as to have different values for different possible values of the labels. This can be used to correct for different link distance densities of labeled variants, for example, where the number of variants labeled benign is significantly higher than the number of variants labeled pathogenic. For example, denote the label vector length by v, so that the label of the labeled variant Lr can be represented as $$L^r = (L_1^r, L_2^r, \ldots, L_v^r).$$

An example is a label that uses a one-hot encoding, where $L^r$ is a binary vector with a 1 in one position and zero everywhere else. The weight $w^{tr}$ for the other variant t and the labeled variant r can be a real-valued vector of the same length, v:

$$w^{tr} = (w_1^{tr}, w_2^{tr}, \ldots, w_v^{tr}).$$

The weights may be determined by applying a weighting module to the link distances, in a way so that different possible values of the labels may have different weights. Using e to index the labels such that e ranges from 1 to v, the weighting module may determine the weights as follows:

$$w_e^{tr} \leftarrow 1/(1 + \alpha_e \ d^{tr}),$$

$$w_e^{tr} \leftarrow \exp(-\alpha_e \ d^{tr}),$$

$$w_e^{tr} \leftarrow \left( \frac{1}{1 + \exp(\alpha_e(d_{0,e} - d^{tr}))} \right),$$

where $\alpha_e$ and $d_{0,e}$ are predetermined numerical parameters that determine how quickly the weights drop off to zero as link distance increases, but in a way that is label dependent. For instance, if the labels are (1,0) for "benign" and (0,1) for "pathogenic" and, for a particular test variant, the link distance density of labeled benign variants is much larger than the density of labeled pathogenic variants nearby in the genome, then $\alpha_1$ and $\alpha_2$ can be set to values such that the weights drop off more quickly with link distance for the benign variants: $\alpha_1 > \alpha_2$. The weights for each label value e=1, ..., q may be separately normalized so that the sum over the labeled variants is one. The weighting module may first compute the un-normalized weights $\tilde{w}_e^{tr}$ independently for different labeled variants, such as by using $$w\tilde{w}_e^{tr} \leftarrow 1/(1 + \alpha_e d^{tr}).$$

Then, for each label value, the weighting module may determine the normalization factor:

$$z_e^t = \sum_{r=1}^R \tilde{w}_e^{tr'} \ ^{for} \ e = 1 \ldots q.$$

Lastly, the weighting module may output the normalized weights:

$$(w_1^{t1}, w_1^{t2}, \ldots, w_1^{tR}) \leftarrow (\tilde{w}_1^{t1}/z_1^t, \tilde{w}_1^{t2}/z_1^t, \ldots, \tilde{w}_1^{tR}/z_1^t)$$

$$(w_q^{t1}, w_q^{t2}, \ldots, w_q^{tR}) \leftarrow (\tilde{w}_q^{t1}/z_q^t, \tilde{w}_q^{t2}/z_q^t, \ldots, \tilde{w}_q^{tR}/z_q^t)$$

It will be appreciated that these computations can be performed differently so as to achieve the same or a very similar effect.

For all label values e=1, ..., q, the eth label of the other variant t may be determined using the weighted average:

$$L_e^t \leftarrow \sum_{r=1}^R w_e^{tr} L_e^r.$$

The weighting module parameters may be set by hand or by searching over appropriate values using a dataset of variants with known labels, such as to obtain the highest possible correct label classification rate.

The link distance may provide information about how similar two variants are in their molecular phenotype, but additional information may be available about the variants that can be used by the weighting module to determine the weights. Additional information may include the proximity of the two variants within the biological sequence, such as the difference in the coordinates of two single-substitution variants; quantitative trait loci information, such as expression- or splicing-quantitative trait loci information; information about the linkage disequilibrium between the two variants or between the two variants and other variants of interest; information pertaining to other information for variants that are implicated in a specific disease or class of diseases. It will be appreciated that other types of information may be used to adjust the weights. This additional information for other variant t and labeled variant r may be denoted by $I^{tr}$.

More generally, the link distance may be determined using a link neural network, which takes as input the molecular phenotype of the labeled variant for contexts c=1, ..., T, $m^r = (m_1^r, \ldots, m_T^r)$, and the molecular phenotype of the other variant for contexts c=1, ..., T, $m^t = (m_1^r, \ldots, m_T^r)$, and the additional information $I^{tr}$, and outputs the link distance $d^{tr}$. Denoting the operations of the link neural network by N( ), the application of the link neural network can be represented as $$d^{tr} \leftarrow N(m^t, m^r, I^{tr}).$$

The parameters of the link neural network may be determined from a dataset of examples, wherein each example consists of the pair of variants, the additional information, and the target, which may be derived from labels for the variants and a measure of similarity on the labels. An appropriate machine learning method can be used to configure the link neural network.

In one embodiment, the link neural network is not trained using a dataset of examples, but is instead configured by hand. For example, if the link neural network is configured as follows, $$N(m^t, m^r, I^{tr}) \leftarrow \sum_{c=1}^T (m_c^t - m_c^r)^2,$$

then it acts to produce the link distance described above.

In another embodiment, the additional information pertains to the proximity of two localized variants, such as single-substitution variants, within the biological sequence. In this case, for one of the other variants, the labeled variants that are nearby in the biological sequence may be given lower link distances, even if their molecular phenotypes are similar Denote the absolute difference in coordinates between the other variant t and the labeled variant r in the biological sequence by $I^{tr}$. If this value is large, the variants are less likely to have similar function, all else being the same, than if the value is small. The link neural network may be configured as follows:

$$N(m^t, m^r, I^{tr}) \leftarrow \sum_{c=1}^T (m_c^t - m_c^r)^2 + \gamma I^{tr},$$

where $\gamma$ is a parameter that trades off the effect of the molecular phenotype distance and the additional information. This parameter may be set using training data. It will be appreciated that other measures of proximity may be used, such as square differences in coordinates, and that other types of additional information may be used. It will be appreciated that multiple types of additional information may be encoded in $I^{ir}$, including real-valued, vector-valued and categorical information, which may be encoded, for instance, using one-hot encoding.

In another aspect, the present disclosure provides methods of using conservation data to train MPNNs. For example, an MPNN may be trained using biological sequences $X^1, X^2, \ldots, X^U$, where U is the number of biological sequences and $X^u$ is the uth biological sequence. The ith symbol in the uth biological sequence may be denoted by $x_i^u$ and it may be represented as described above or using a different method. Suppose the molecular phenotype value corresponding to the sequence is $m^u$. Training data may comprise $X^1, X^2, \ldots, X^U$ and $m^1, m^2, \ldots, m^U$. Once trained, the MPNN may take $X^u$ as input and output a molecular phenotype value (or set of values) that has a small discrepancy compared to $m^u$.

It may be assumed that there are also conservation levels available for at least one element in at least one of the training sequences for training. Conservation levels for sequence $X^u$ may be denoted by $c_1^u, c_2^u, \ldots, c_n^u$ where the sequence has length n. The conservation levels may be appended to the molecular phenotype $m^u$ to form an expanded training target, $m^u, c_1^u, c_2^u, \ldots, c_n^u$. That is, once trained, the system can take as input a sequence $X^u$ and output values that have low discrepancy with the expanded target $m^u, c_1^u, c_2^u, \ldots, c_n^u$.

This form of training may encourage intermediate computations, or intermediate layers, of the MPNN to find representations that are both good at predicting the conservation values and also at predicting the molecular phenotype. The reason this is helpful may be made evident by an example. Suppose that there are two sequence patterns that are both correlated with the desired molecular phenotype and during training, the MPNN may choose between the two patterns. If one of the patterns is also correlated with conservation, the MPNN may select that pattern over the other one, since the MPNN may also determine a conservation value. As stated above, biological sequence elements that are conserved are more likely to be functional, so, everything else being equal, it is best for the MPNN to select the sequence pattern that is correlated with conservation.

At test time, when a new biological sequence is to be evaluated, the conservation elements for that sequence may not be required. The sequence can be fed into the MPNN, and it will output a value for the molecular phenotype.

In one embodiment, the MPNN has a single intermediate (hidden) layer of values and that layer of values is used to determine both the molecular phenotype and the conservation levels.

In another embodiment, the MPNN has more than one intermediate layer and the last layer is used to determine both the molecular phenotype and the conservation levels.

In another embodiment, the MPNN has more than one intermediate layer and different layers are used to determine the molecular phenotype and the conservation levels.

In another embodiment, the layer representing the conservation values is also used to determine the molecular phenotype.

One of ordinary skill in the art will appreciate the following embodiments. First, conservation values need not be present for all sequences or for all symbols within each sequence. Second, different types of neural networks may be used, including, but not limited to convolutional neural networks, autoencoders, long-term short-term memory neural networks, recursive neural networks, decision trees, and support vector machines (SVMs). Third, different cost functions may be used to train the neural network. Fourth, the cost function used for training may allocate a different overall cost to the conservation values than to the molecular phenotype. Fifth, the molecular phenotype may be represented in different ways, including as a binary value, a real value, a set of binary or real values, a probability distribution, or a set of probability distributions. Sixth, the input sequence may be represented in different ways. Seventh, different kinds of regularization may be used during training, such as weight penalties and dropout. Finally, training may operate in batch mode, minibatch mode, using stochastic online gradient descent, or other methods or combinations thereof.

Figure 13:
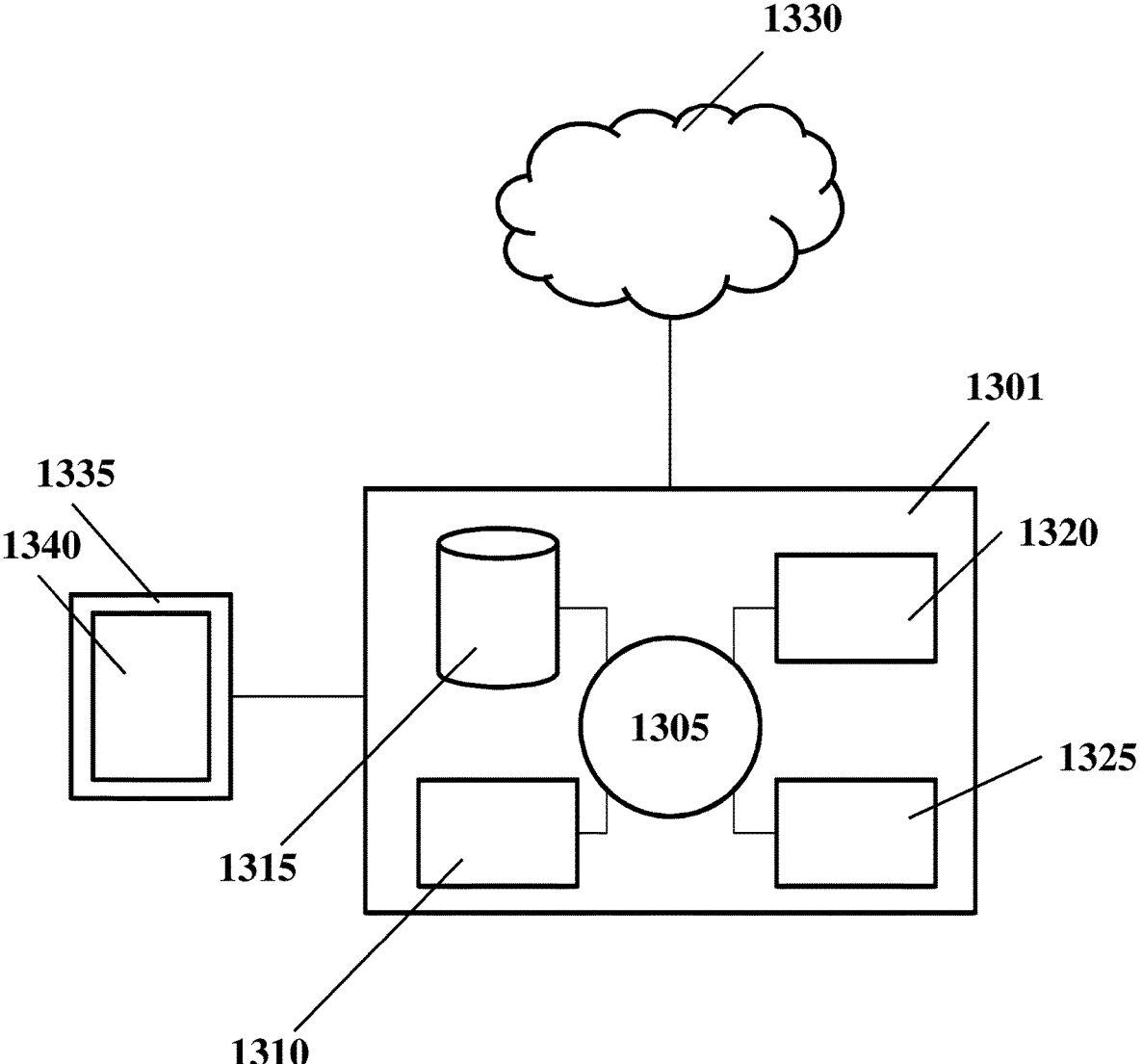
FIG. 13 shows a computer system that is programmed or otherwise configured to implement methods provided herein.

FIG. 13 shows a computer system 1301 that is programmed or otherwise configured to implement methods provided herein.

The computer system 1301 may be programmed or otherwise configured to implement architectures for training neural networks using biological sequences, conservation, and molecular phenotypes. The computer system 1301 can regulate various aspects of the present disclosure, such as, for example, training a neural network using biological sequences, conservation, and molecular phenotypes. The computer system 1301 can be an electronic device of a user or a computer system that is remotely located with respect to the electronic device. The electronic device can be a mobile electronic device.

The computer system 1301 includes a central processing unit (CPU, also "processor" and "computer processor" herein) 1305, which can be a single core or multi core processor, or a plurality of processors for parallel processing. The computer system 1301 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The computer system 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the computer system 1301, can implement a peer-to-peer network, which may enable devices coupled to the computer system 1301 to behave as a client or a server.

The CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and writeback.

The CPU 1305 can be part of a circuit, such as an integrated circuit. One or more other components of the system 1301 can be included in the circuit. In some cases, the circuit is an application specific integrated circuit (ASIC).

The storage unit 1315 can store files, such as drivers, libraries and saved programs. The storage unit 1315 can store user data, e.g., user preferences and user programs. The computer system 1301 in some cases can include one or more additional data storage units that are external to the computer system 1301, such as located on a remote server that is in communication with the computer system 1301 through an intranet or the Internet.

The computer system 1301 can communicate with one or more remote computer systems through the network 1330. For instance, the computer system 1301 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1301 via the network 1330.

Methods as described herein can be implemented by way of machine (e.g., computer processor) executable code stored on an electronic storage location of the computer system 1301, such as, for example, on the memory 1310 or electronic storage unit 1315. The machine executable or machine readable code can be provided in the form of software. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1301 can include or be in communication with an electronic display 1335 that comprises a user interface (UI) 1340. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1305. The algorithm can, for example, implement architectures to train a neural network using biological sequences, conservation, and molecular phenotypes.

Although the description has been described with respect to particular embodiments thereof, these particular embodiments are merely illustrative, and not restrictive. Concepts illustrated in the examples may be applied to other examples and implementations.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for training a neural network for processing a test biological sequence, the method comprising:

(a) providing the neural network, wherein the neural network comprises at least one intermediate layer and is configured to process an input biological sequence to determine output data comprising:

(i) a molecular phenotype corresponding to the input biological sequence, wherein the molecular phenotype comprises a numerical value which quantifies biological molecules of cells, and (ii) a conservation value corresponding to each element of a plurality of elements of the input biological sequence;

(b) providing a training data set comprising:

(i) a set of input biological sequences, and (ii) for each input biological sequence in the set of input biological sequences, label data comprising:

(1) a molecular phenotype corresponding to the input biological sequence, and (2) a conservation value corresponding to each element of a plurality of elements of the input biological sequence;

(c) using the training data set to configure a set of parameters of the neural network, such that a total loss of the training data set is minimized based at least in part on minimizing (i) a total loss of the molecular phenotypes and (ii) a total loss of the conservation values, thereby generating a trained neural network; and (d) processing the test biological sequence using the trained neural network, wherein the processing comprises providing the test biological sequence to the trained neural network, to determine a molecular phenotype corresponding to the test biological sequence and a conservation value corresponding to each test element of a plurality of test elements of the test biological sequence.

2. The method of claim 1, wherein the trained neural network comprises a single intermediate layer configured to determine the molecular phenotype and the conservation value corresponding to each test element of the plurality of test elements of the test biological sequence.

3. The method of claim 1, wherein the trained neural network comprises a plurality of intermediate layers, wherein a last layer of the plurality of intermediate layers is configured to determine the molecular phenotype and the conservation value corresponding to each test element of the plurality of test elements of the test biological sequence.

4. The method of claim 1, wherein the trained neural network comprises a plurality of intermediate layers, wherein a first layer of the plurality of intermediate layers is configured to determine the molecular phenotype corresponding to the test biological sequence, and wherein a second layer of the plurality of intermediate layers is configured to determine the conservation value corresponding to each test element of the plurality of test elements of the test biological sequence.

5. The method of claim 1, wherein the molecular phenotype corresponding to the test biological sequence is determined based at least in part on the conservation value corresponding to each test element of the plurality of test elements of the test biological sequence determined using the trained neural network.

6. The method of claim 1, wherein the input biological sequences comprise deoxyribonucleic acid (DNA) sequences, ribonucleic acid (RNA) sequences, or protein sequences.

7. The method of claim 1, wherein the input biological sequences comprise a genetic variant as compared to a reference genome, wherein the genetic variant comprises a substitution, an insertion, a deletion, or a combination thereof.

8. The method of claim 7, wherein the genetic variant is selected from the group consisting of a nucleotide variant, a single base substitution, a copy number variation (CNV), a single nucleotide variant (SNV), an insertion or deletion (indel), a fusion, a transversion, a translocation, an inversion, a duplication, an amplification, a truncation, and a combination thereof.

9. The method of claim 1, wherein the molecular phenotypes comprise a level or a percentage of transcripts that include an exon, a level or a percentage of transcripts that use an alternative splice site, a level or a percentage of transcripts that use an alternative polyadenylation site, an affinity of an RNA-protein interaction, an affinity of a DNA-protein interaction, a specificity of an RNA-binding protein, a specificity of a DNA-binding protein, a specificity of a microRNA-RNA interaction, a level of protein phosphorylation, a phosphorylation pattern, a distribution of proteins along a strand of DNA containing a gene, a number of copies of gene transcripts, a distribution of proteins along a transcript, a number of proteins, or a combination thereof.

10. The method of claim 1, wherein the input biological sequence is a nucleotide sequence.

11. The method of claim 1, wherein the element of the plurality of elements is a nucleotide.

12. A system for training a neural network for processing a test biological sequence, the system comprising:

a data storage unit comprising a training data set comprising (i) a set of input biological sequences, and (ii) for each input biological sequence in the set of input biological sequences, label data comprising: (1) a molecular phenotype corresponding to the input biological sequence, and (2) a conservation value corresponding to each element of a plurality of elements of the input biological sequence; and one or more computer processors operatively coupled to the data storage unit, wherein the one or more computer processors are individually or collectively programmed to:

(a) provide the neural network, wherein the neural network comprises at least one intermediate layer and is configured to process an input biological sequence to determine output data comprising:

(i) a molecular phenotype corresponding to the input biological sequence, wherein the molecular phenotype comprises a numerical value which quantifies biological molecules of cells, and (ii) a conservation value corresponding to each element of a plurality of elements of the input biological sequence;

(b) use the training data set to configure a set of parameters of the neural network, such that a total loss of the training data set is minimized at least in part by minimizing (i) a total loss of the molecular phenotypes and (ii) a total loss of the conservation values, thereby generating a trained neural network; and (c) provide the trained neural network with a test biological sequence, wherein the trained neural network is configured to determine a molecular phenotype corresponding to the test biological sequence and a conservation value corresponding to each test element of the plurality of test elements of the test biological sequence.

13. The system of claim 12, wherein the trained neural network comprises a single intermediate layer configured to determine the molecular phenotype and the conservation value corresponding to each test element of the plurality of test elements of the test biological sequence.

14. The system of claim 12, wherein the trained neural network comprises a plurality of intermediate layers, wherein a last layer of the plurality of intermediate layers is configured to determine the molecular phenotype and the conservation value corresponding to each test element of the plurality of test elements of the test biological sequence.

15. The system of claim 12, wherein the trained neural network comprises a plurality of intermediate layers, wherein a first layer of the plurality of intermediate layers is configured to determine the molecular phenotype corresponding to the test biological sequence, and wherein a second layer of the plurality of intermediate layers is configured to determine the conservation value corresponding to each test element of the plurality of test elements of the test biological sequence.

16. The system of claim 12, wherein the one or more computer processors are individually or collectively programmed to further determine the molecular phenotype corresponding to the test biological sequence based at least in part on the conservation value corresponding to each test element of the plurality of test elements of the test biological sequence determined using the trained neural network.

17. The system of claim 12, wherein the input biological sequences comprise deoxyribonucleic acid (DNA) sequences, ribonucleic acid (RNA) sequences, or protein sequences.

18. The system of claim 12, wherein the input biological sequences comprise a genetic variant as compared to a reference genome, wherein the genetic variant comprises a substitution, an insertion, a deletion, or a combination thereof.

19. The system of claim 18, wherein the genetic variant is selected from the group consisting of a nucleotide variant, a single base substitution, a copy number variation (CNV), a single nucleotide variant (SNV), an insertion or deletion (indel), a fusion, a transversion, a translocation, an inversion, a duplication, an amplification, a truncation, and a combination thereof.

20. The system of claim 12, wherein the molecular phenotypes comprises a level or a percentage of transcripts that include an exon, a level or a percentage of transcripts that use an alternative splice site, a level or a percentage of transcripts that use an alternative polyadenylation site, an affinity of an RNA-protein interaction, an affinity of a DNA-protein interaction, a specificity of an RNA-binding protein, a specificity of a DNA-binding protein, a specificity of a microRNA-RNA interaction, a level of protein phosphorylation, a phosphorylation pattern, a distribution of proteins along a strand of DNA containing a gene, a number of copies of gene transcripts, a distribution of proteins along a transcript, a number of proteins, or a combination thereof.

21. The system of claim 12, wherein the input biological sequence is a nucleotide sequence.

22. The system of claim 12, wherein the element of the plurality of elements is a nucleotide.

* * * * *